US012496066B2

(12) United States Patent
Patel et al.

(10) Patent No.: US 12,496,066 B2
(45) Date of Patent: Dec. 16, 2025

(54) SURGICAL STAPLER HANDLE ASSEMBLY HAVING ACTUATION MECHANISM WITH LONGITUDINALLY ROTATABLE SHAFT

(71) Applicant: Applied Medical Resources Corporation, Rancho Santa Margarita, CA (US)

(72) Inventors: Atal C. Patel, Mission Viejo, CA (US); Jonathan Covach, Mission Viejo, CA (US); Christina N. Reed, Trabuco Canyon, CA (US); Gary M. Johnson, Rancho Santa Margarita, CA (US); Matthew M. Becerra, Lake Forest, CA (US)

(73) Assignee: Applied Medical Resources Corportion, Rancho Santa Margarita, CA (US)

( * ) Notice: Subject to any disclaimer, the term of this patent is extended or adjusted under 35 U.S.C. 154(b) by 0 days.

(21) Appl. No.: 18/904,385

(22) Filed: Oct. 2, 2024

(65) Prior Publication Data

US 2025/0025171 A1 Jan. 23, 2025

Related U.S. Application Data

(63) Continuation of application No. 18/494,610, filed on Oct. 25, 2023, now Pat. No. 12,137,907, which is a (Continued)

(51) Int. Cl.

*A61B 17/072* (2006.01)
*A61B 17/00* (2006.01)
*A61B 17/068* (2006.01)

(52) U.S. Cl.

CPC *A61B 17/07207* (2013.01); *A61B 2017/0046* (2013.01); *A61B 2017/00477* (2013.01); *A61B 17/068* (2013.01); *A61B 2017/07257* (2013.01)

(58) Field of Classification Search

CPC ............ A61B 17/07207; A61B 17/068; A61B 2017/0046; A61B 2017/00477; A61B 2017/07257

See application file for complete search history.

(56) References Cited

U.S. PATENT DOCUMENTS 2,073,960 A 3/1937 Crosby
2,140,593 A 12/1938 Pankonin
(Continued)

FOREIGN PATENT DOCUMENTS

EP 0 251 444 A1 1/1988
EP 0 492 283 A1 7/1992
(Continued)

OTHER PUBLICATIONS

Ethicon Endo Surgery, Inc., Contour Curved Cutter Stapler, 2014.
(Continued)

*Primary Examiner* — Eronica Martin
(74) *Attorney, Agent, or Firm* — John F. Heal

(57) ABSTRACT

A handle assembly for a surgical stapler can comprise a rotatable actuation shaft. The actuation shaft can have a first rotational orientation in which it can actuate a jaw assembly in a repeatable open and close mode, a second rotational orientation in which it can actuate a jaw assembly in a staple firing mode, and a third rotational orientation in which it can actuate a jaw assembly in a reversing mode. The handle assembly can include a rotational mechanism arranged to discretely position the rotatable actuation shaft in one of the rotational orientations. The rotational mechanism can be arranged for single handed operation such as by including a slidable switch or selector to rotate the actuation shaft.

17 Claims, 18 Drawing Sheets

Related U.S. Application Data continuation of application No. 17/980,395, filed on Nov. 3, 2022, now Pat. No. 11,844,491, which is a continuation of application No. 17/141,050, filed on Jan. 4, 2021, now Pat. No. 11,529,141, which is a continuation of application No. 16/789,152, filed on Feb. 12, 2020, now Pat. No. 10,912,565, which is a continuation of application No. 15/598,458, filed on May 18, 2017, now Pat. No. 10,595,866, which is a continuation of application No. 14/213,493, filed on Mar. 14, 2014, now Pat. No. 9,668,732.

(60) Provisional application No. 61/794,700, filed on Mar. 15, 2013.

(56) References Cited

U.S. PATENT DOCUMENTS

| | | | |
|---|---|---|---|
| 2,351,608 | A | 6/1944 | Greenwood |
| 2,487,565 | A | 11/1949 | Leber et al. |
| 2,641,154 | A | 6/1953 | Heller |
| 3,076,373 | A | 2/1963 | Matthews |
| 3,077,812 | A | 2/1963 | Dietrich |
| 3,080,564 | A | 3/1963 | Strekopitov et al. |
| 3,203,220 | A | 8/1965 | Kaepernik |
| 3,252,643 | A | 5/1966 | Strekopitov et al. |
| 3,273,562 | A | 9/1966 | Brown |
| 3,373,646 | A | 3/1968 | Ehlert |
| 3,459,187 | A | 8/1969 | Pallotta |
| 3,494,533 | A | 2/1970 | Green et al. |
| 3,662,939 | A | 5/1972 | Bryan |
| 3,675,688 | A | 7/1972 | Bryan et al. |
| 3,692,224 | A | 9/1972 | Astafiev et al. |
| 4,261,244 | A | 4/1981 | Becht et al. |
| 4,281,785 | A | 8/1981 | Brooks |
| 4,304,236 | A | 12/1981 | Conta et al. |
| 4,312,363 | A | 1/1982 | Rothfuss et al. |
| 4,317,451 | A | 3/1982 | Cerwin et al. |
| 4,407,286 | A | 10/1983 | Noiles et al. |
| 4,434,796 | A | 3/1984 | Karapetian et al. |
| 4,442,964 | A | 4/1984 | Becht |
| 4,454,875 | A | 6/1984 | Pratt et al. |
| 4,522,327 | A | 6/1985 | Korthoff et al. |
| 4,527,724 | A | 7/1985 | Chow et al. |
| 4,589,582 | A | 5/1986 | Bilotti |
| 4,591,085 | A | 5/1986 | Di Giovanni |
| 4,606,344 | A | 8/1986 | Di Giovanni |
| 4,608,981 | A | 9/1986 | Rothfuss et al. |
| 4,610,383 | A | 9/1986 | Rothfuss et al. |
| 4,728,020 | A | 3/1988 | Green et al. |
| 4,805,823 | A | 2/1989 | Rothfuss |
| 4,892,244 | A | 1/1990 | Fox et al. |
| 4,923,350 | A | 5/1990 | Hinksman et al. |
| 4,941,623 | A | 7/1990 | Pruitt |
| 4,955,959 | A | 9/1990 | Tompkins et al. |
| 4,978,049 | A | 12/1990 | Green |
| 5,031,814 | A | 7/1991 | Tompkins et al. |
| 5,065,929 | A | 11/1991 | Schulze et al. |
| 5,071,052 | A | 12/1991 | Rodak et al. |
| 5,106,008 | A | 4/1992 | Tompkins et al. |
| 5,116,349 | A | 5/1992 | Aranyi |
| 5,129,570 | A | 7/1992 | Schulze et al. |
| 5,201,746 | A | 4/1993 | Shichman |
| 5,221,036 | A | 6/1993 | Takase |
| 5,236,440 | A | 8/1993 | Hlavacek |
| 5,240,163 | A | 8/1993 | Stein et al. |
| RE34,519 | E | 1/1994 | Fox et al. |
| 5,275,323 | A | 1/1994 | Schulze et al. |
| 5,289,963 | A | 3/1994 | McGarry et al. |
| D347,474 | S | 5/1994 | Olson |
| 5,307,976 | A | 5/1994 | Olson et al. |
| 5,308,576 | A | 5/1994 | Green et al. |
| 5,326,013 | A | 7/1994 | Green et al. |
| 5,350,400 | A | 9/1994 | Esposito et al. |
| 5,360,305 | A | 11/1994 | Kerrigan |
| 5,364,002 | A | 11/1994 | Green et al. |
| 5,366,479 | A | 11/1994 | McGarry et al. |
| 5,381,943 | A | 1/1995 | Allen et al. |
| 5,389,098 | A | 2/1995 | Tsuruta et al. |
| 5,395,034 | A | 3/1995 | Allen et al. |
| 5,397,046 | A | 3/1995 | Savage et al. |
| 5,413,267 | A | 5/1995 | Solyntjes et al. |
| 5,415,334 | A | 5/1995 | Williamson, IV et al. |
| 5,415,335 | A | 5/1995 | Knodell, Jr. |
| 5,439,155 | A | 8/1995 | Viola |
| 5,439,479 | A | 8/1995 | Shichman et al. |
| 5,445,304 | A | 8/1995 | Plyley et al. |
| 5,447,265 | A | 9/1995 | Vidal et al. |
| 5,452,836 | A | 9/1995 | Huitema et al. |
| 5,456,401 | A | 10/1995 | Green et al. |
| 5,458,279 | A | 10/1995 | Plyley |
| 5,462,215 | A | 10/1995 | Viola et al. |
| 5,464,144 | A | 11/1995 | Guy et al. |
| 5,465,895 | A | 11/1995 | Knodel et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,472,132 | A | 12/1995 | Savage et al. |
| 5,480,089 | A | 1/1996 | Blewett |
| 5,485,952 | A | 1/1996 | Fontayne |
| 5,487,500 | A | 1/1996 | Knodel et al. |
| 5,489,058 | A | 2/1996 | Plyley |
| 5,497,933 | A | 3/1996 | DeFonzo et al. |
| 5,507,426 | A | 4/1996 | Young et al. |
| 5,507,773 | A | 4/1996 | Hultema et al. |
| 5,509,596 | A | 4/1996 | Green et al. |
| 5,509,920 | A | 4/1996 | Phillips et al. |
| 5,529,235 | A | 6/1996 | Boiarski et al. |
| 5,547,117 | A | 8/1996 | Hamblin et al. |
| 5,553,765 | A | 9/1996 | Knodel et al. |
| 5,554,164 | A | 9/1996 | Wilson et al. |
| 5,558,266 | A | 9/1996 | Green et al. |
| 5,562,241 | A | 10/1996 | Knodel et al. |
| 5,562,700 | A | 10/1996 | Huitema et al. |
| 5,562,701 | A | 10/1996 | Huitema et al. |
| 5,562,702 | A | 10/1996 | Huitema et al. |
| 5,564,615 | A | 10/1996 | Bishop et al. |
| 5,571,115 | A | 11/1996 | Nicholas |
| 5,571,285 | A | 11/1996 | Chow et al. |
| 5,579,978 | A | 12/1996 | Green et al. |
| 5,580,067 | A | 12/1996 | Hamblin et al. |
| 5,584,425 | A | 12/1996 | Savage et al. |
| 5,586,711 | A | 12/1996 | Plyley et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,605,272 | A | 2/1997 | Witt et al. |
| 5,607,095 | A | 3/1997 | Smith et al. |
| 5,615,820 | A | 4/1997 | Viola |
| 5,626,587 | A | 5/1997 | Bishop et al. |
| 5,630,539 | A | 5/1997 | Plyley et al. |
| 5,634,584 | A | 6/1997 | Okorocha et al. |
| 5,636,779 | A | 6/1997 | Palmer |
| 5,657,921 | A | 8/1997 | Young et al. |
| 5,662,258 | A | 9/1997 | Knodel et al. |
| 5,662,662 | A | 9/1997 | Bishop et al. |
| 5,662,667 | A | 9/1997 | Knodel |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,678,748 | A | 10/1997 | Plyley |
| 5,680,982 | A | 10/1997 | Schulze et al. |
| 5,680,983 | A | 10/1997 | Plyley et al. |
| 5,697,542 | A | 12/1997 | Knodel et al. |
| 5,697,543 | A | 12/1997 | Burdorff |
| 5,704,534 | A | 1/1998 | Huitema et al. |
| 5,704,898 | A | 1/1998 | Kokish |
| 5,706,998 | A | 1/1998 | Blyley et al. |
| 5,709,334 | A | 1/1998 | Sorrentino et al. |
| 5,713,505 | A | 2/1998 | Huitema |
| 5,715,988 | A | 2/1998 | Palmer |
| 5,718,359 | A | 2/1998 | Palmer et al. |

(56) References Cited

U.S. PATENT DOCUMENTS

| | | | |
|---|---|---|---|
| 5,732,871 | A | 3/1998 | Clark et al. |
| 5,735,445 | A | 4/1998 | Vidal et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,782,397 | A | 7/1998 | Koukline |
| 5,785,232 | A | 7/1998 | Vidal et al. |
| 5,794,834 | A | 8/1998 | Hamblin et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,240 | A | 9/1998 | Robertson |
| 5,814,055 | A | 9/1998 | Knodel et al. |
| 5,820,009 | A | 10/1998 | Melling et al. |
| 5,829,662 | A | 11/1998 | Allen et al. |
| 5,860,995 | A | 1/1999 | Berkelaar |
| 5,865,361 | A | 2/1999 | Milliman et al. |
| 5,878,937 | A | 3/1999 | Green et al. |
| 5,878,938 | A | 3/1999 | Bittner et al. |
| 5,893,506 | A | 4/1999 | Powell |
| 5,894,979 | A | 4/1999 | Powell |
| 5,901,895 | A | 5/1999 | Heaton et al. |
| 5,918,791 | A | 7/1999 | Sorrentino et al. |
| 5,931,847 | A | 8/1999 | Bittner et al. |
| 5,954,259 | A | 9/1999 | Viola et al. |
| 5,964,394 | A | 10/1999 | Robertson |
| D416,089 | S | 11/1999 | Barton et al. |
| 5,988,479 | A | 11/1999 | Palmer |
| 6,032,849 | A | 3/2000 | Mastri et al. |
| 6,053,390 | A | 4/2000 | Green et al. |
| 6,079,606 | A | 6/2000 | Milliman et al. |
| 6,109,500 | A | 8/2000 | Alli et al. |
| 6,131,789 | A | 10/2000 | Schulze et al. |
| 6,155,473 | A | 12/2000 | Tompkins et al. |
| D441,865 | S | 5/2001 | Racenet et al. |
| 6,241,139 | B1 | 6/2001 | Milliman et al. |
| 6,250,532 | B1 | 6/2001 | Green et al. |
| 6,264,087 | B1 | 7/2001 | Whitman |
| 6,270,453 | B1 | 8/2001 | Sakai |
| 6,325,810 | B1 | 12/2001 | Hamilton et al. |
| 6,330,965 | B1 | 12/2001 | Milliman et al. |
| 6,488,196 | B1 | 12/2002 | Fenton, Jr. |
| 6,550,757 | B2 | 4/2003 | Sesek |
| 6,569,171 | B2 | 5/2003 | DeGuillebon et al. |
| 6,595,509 | B2 | 7/2003 | Sesek |
| 6,619,529 | B2 | 9/2003 | Green et al. |
| 6,644,532 | B2 | 11/2003 | Green et al. |
| 6,669,073 | B2 | 12/2003 | Milliman et al. |
| 6,716,233 | B1 | 4/2004 | Whitman |
| 6,786,382 | B1 | 9/2004 | Hoffman |
| 6,817,508 | B1 | 11/2004 | Racenet et al. |
| 6,821,282 | B2 | 11/2004 | Perry et al. |
| 6,835,199 | B2 | 12/2004 | McGuckin, Jr. et al. |
| 6,913,181 | B2 | 7/2005 | Mochizuki et al. |
| 6,923,360 | B2 | 8/2005 | Sesek et al. |
| 6,953,138 | B1 | 10/2005 | Dworak et al. |
| 6,953,139 | B2 | 10/2005 | Milliman et al. |
| 6,964,363 | B2 | 11/2005 | Wales et al. |
| 6,978,921 | B2 | 12/2005 | Shelton, IV et al. |
| 6,986,451 | B1 | 1/2006 | Mastri et al. |
| 6,988,649 | B2 | 1/2006 | Shelton, IV et al. |
| 7,000,818 | B2 | 2/2006 | Shelton, IV et al. |
| 7,044,352 | B2 | 5/2006 | Shelton, IV et al. |
| 7,044,353 | B2 | 5/2006 | Mastri et al. |
| 7,044,947 | B2 | 5/2006 | de la Torre et al. |
| 7,055,730 | B2 | 6/2006 | Ehrenfels et al. |
| 7,070,083 | B2 | 7/2006 | Jankowski |
| 7,097,089 | B2 | 8/2006 | Marczyk |
| 7,097,650 | B2 | 8/2006 | Weller et al. |
| 7,108,472 | B2 | 9/2006 | Norris et al. |
| 7,128,253 | B2 | 10/2006 | Mastri et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,147,139 | B2 | 12/2006 | Schwemberger et al. |
| 7,213,736 | B2 | 5/2007 | Wales et al. |
| 7,225,964 | B2 | 6/2007 | Mastri et al. |
| 7,237,708 | B1 | 7/2007 | Guy et al. |
| 7,258,262 | B2 | 8/2007 | Mastri et al. |
| 7,275,674 | B2 | 10/2007 | Racenet et al. |
| 7,278,562 | B2 | 10/2007 | Mastri et al. |
| 7,290,692 | B2 | 11/2007 | Marks |
| 7,293,685 | B2 | 11/2007 | Ehrenfels et al. |
| 7,303,107 | B2 | 12/2007 | Milliman et al. |
| 7,308,998 | B2 | 12/2007 | Mastri et al. |
| 7,328,828 | B2 | 2/2008 | Ortiz et al. |
| 7,334,717 | B2 | 2/2008 | Rethy et al. |
| 7,380,695 | B2 | 6/2008 | Doll et al. |
| 7,380,696 | B2 | 6/2008 | Shelton, IV et al. |
| 7,398,908 | B2 | 7/2008 | Holsten et al. |
| 7,399,310 | B2 | 7/2008 | Edoga et al. |
| 7,401,721 | B2 | 7/2008 | Holsten et al. |
| 7,404,508 | B2 | 7/2008 | Smith et al. |
| 7,407,075 | B2 | 8/2008 | Holsten et al. |
| 7,407,078 | B2 | 8/2008 | Shelton, IV et al. |
| 7,416,101 | B2 | 8/2008 | Shelton, IV et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,422,136 | B1 | 9/2008 | Marczyk |
| 7,422,139 | B2 | 9/2008 | Shelton, IV et al. |
| 7,431,188 | B1 | 10/2008 | Marczyk |
| 7,434,715 | B2 | 10/2008 | Shelton, IV et al. |
| 7,434,716 | B2 | 10/2008 | Viola |
| 7,455,208 | B2 | 11/2008 | Wales et al. |
| 7,455,676 | B2 | 11/2008 | Holsten et al. |
| 7,461,767 | B2 | 12/2008 | Viola et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,481,348 | B2 | 1/2009 | Marczyk |
| 7,481,349 | B2 | 1/2009 | Holsten et al. |
| 7,487,899 | B2 | 2/2009 | Shelton, IV et al. |
| 7,490,749 | B2 | 2/2009 | Schall et al. |
| 7,506,790 | B2 | 3/2009 | Shelton, IV |
| 7,506,791 | B2 | 3/2009 | Omaits et al. |
| 7,513,408 | B2 | 4/2009 | Shelton, IV et al. |
| 7,530,484 | B1 | 5/2009 | Durrani |
| 7,543,730 | B1 | 6/2009 | Marczyk |
| 7,543,731 | B2 | 6/2009 | Green et al. |
| 7,546,940 | B2 | 6/2009 | Milliman et al. |
| 7,549,564 | B2 | 6/2009 | Boudreaux |
| 7,552,854 | B2 | 6/2009 | Wixey et al. |
| 7,556,186 | B2 | 7/2009 | Milliman |
| 7,565,993 | B2 | 7/2009 | Milliman et al. |
| 7,568,604 | B2 | 8/2009 | Ehrenfels et al. |
| 7,588,174 | B2 | 9/2009 | Holsten et al. |
| 7,588,175 | B2 | 9/2009 | Timm et al. |
| 7,588,177 | B2 | 9/2009 | Racenet |
| 7,604,151 | B2 | 10/2009 | Hess et al. |
| 7,611,038 | B2 | 11/2009 | Racenet et al. |
| 7,617,961 | B2 | 11/2009 | Viola |
| 7,624,902 | B2 | 12/2009 | Marczyk et al. |
| 7,631,793 | B2 | 12/2009 | Rethy et al. |
| 7,635,074 | B2 | 12/2009 | Olson et al. |
| 7,637,409 | B2 | 12/2009 | Marczyk |
| 7,637,410 | B2 | 12/2009 | Marczyk |
| 7,641,091 | B2 | 1/2010 | Olson et al. |
| 7,641,093 | B2 | 1/2010 | Doll et al. |
| 7,641,095 | B2 | 1/2010 | Viola |
| 7,644,848 | B2 | 1/2010 | Swayze et al. |
| 7,648,055 | B2 | 1/2010 | Marczyk |
| 7,651,017 | B2 | 1/2010 | Ortiz et al. |
| 7,654,431 | B2 | 2/2010 | Hueil et al. |
| 7,658,311 | B2 | 2/2010 | Boudreaux |
| 7,665,647 | B2 | 2/2010 | Shelton, IV et al. |
| 7,669,746 | B2 | 3/2010 | Shelton, IV |
| 7,670,334 | B2 | 3/2010 | Hueil et al. |

(56) References Cited

U.S. PATENT DOCUMENTS

| | | | |
|---|---|---|---|
| 7,673,781 | B2 | 3/2010 | Swayze et al. |
| 7,682,367 | B2 | 3/2010 | Shah et al. |
| 7,690,547 | B2 | 4/2010 | Racenet et al. |
| 7,703,653 | B2 | 4/2010 | Shah et al. |
| 7,717,312 | B2 | 5/2010 | Beetel |
| 7,721,931 | B2 | 5/2010 | Shelton, IV et al. |
| 7,721,933 | B2 | 5/2010 | Ehrenfels et al. |
| 7,721,935 | B2 | 5/2010 | Racenet et al. |
| 7,721,936 | B2 | 5/2010 | Shelton, IV et al. |
| 7,726,538 | B2 | 6/2010 | Holsten et al. |
| 7,726,539 | B2 | 6/2010 | Holsten et al. |
| 7,731,073 | B2 | 6/2010 | Wixey et al. |
| 7,735,703 | B2 | 6/2010 | Morgan et al. |
| 7,753,245 | B2 | 7/2010 | Boudreaux et al. |
| 7,753,246 | B2 | 7/2010 | Scirica |
| 7,757,925 | B2 | 7/2010 | Viola et al. |
| 7,766,210 | B2 | 8/2010 | Shelton, IV et al. |
| 7,770,774 | B2 | 8/2010 | Mastri et al. |
| 7,780,054 | B2 | 8/2010 | Wales |
| 7,780,055 | B2 | 8/2010 | Scirica et al. |
| 7,784,662 | B2 | 8/2010 | Wales et al. |
| 7,784,663 | B2 | 8/2010 | Shelton, IV |
| 7,793,812 | B2 | 9/2010 | Moore et al. |
| 7,798,386 | B2 | 9/2010 | Schall et al. |
| 7,810,693 | B2 | 10/2010 | Broehl et al. |
| 7,815,090 | B2 | 10/2010 | Marczyk |
| 7,815,091 | B2 | 10/2010 | Marczyk |
| 7,819,298 | B2 | 10/2010 | Hall et al. |
| 7,819,896 | B2 | 10/2010 | Racenet |
| 7,823,760 | B2 | 11/2010 | Zemlok et al. |
| 7,828,188 | B2 | 11/2010 | Jankowski |
| 7,828,189 | B2 | 11/2010 | Holsten et al. |
| 7,837,079 | B2 | 11/2010 | Holsten et al. |
| 7,837,081 | B2 | 11/2010 | Holsten et al. |
| 7,845,534 | B2 | 12/2010 | Viola et al. |
| 7,845,535 | B2 | 12/2010 | Scircia |
| 7,845,537 | B2 | 12/2010 | Shelton, IV et al. |
| 7,857,184 | B2 | 12/2010 | Viola |
| 7,857,185 | B2 | 12/2010 | Swayze et al. |
| 7,857,187 | B2 | 12/2010 | Milliman |
| 7,861,906 | B2 | 1/2011 | Doll et al. |
| 7,866,525 | B2 | 1/2011 | Scirica |
| 7,866,527 | B2 | 1/2011 | Hall et al. |
| 7,891,534 | B2 | 2/2011 | Wenchell et al. |
| 7,905,381 | B2 | 3/2011 | Baxter,III et al. |
| 7,909,220 | B2 | 3/2011 | Viola |
| 7,909,221 | B2 | 3/2011 | Viola et al. |
| 7,913,891 | B2 | 3/2011 | Doll et al. |
| 7,914,543 | B2 | 3/2011 | Roth et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,922,063 | B2 | 4/2011 | Zemlok et al. |
| 7,934,628 | B2 | 5/2011 | Wenchell et al. |
| 7,934,629 | B2 | 5/2011 | Wixey et al. |
| 7,934,630 | B2 | 5/2011 | Shelton, IV et al. |
| 7,942,300 | B2 | 5/2011 | Rethy et al. |
| 7,954,685 | B2 | 6/2011 | Viola |
| 7,954,686 | B2 | 6/2011 | Baxter, III et al. |
| 7,959,050 | B2 | 6/2011 | Smith et al. |
| 7,963,433 | B2 | 6/2011 | Whitman et al. |
| 7,992,758 | B2 | 8/2011 | Whitman et al. |
| 8,002,795 | B2 | 8/2011 | Beetel |
| 8,006,887 | B2 | 8/2011 | Marczyk |
| 8,007,513 | B2 | 8/2011 | Nalagatla et al. |
| 8,008,598 | B2 | 8/2011 | Whitman et al. |
| 8,011,550 | B2 | 9/2011 | Aranyi et al. |
| 8,011,553 | B2 | 9/2011 | Mastri et al. |
| 8,012,170 | B2 | 9/2011 | Whitman et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,885 | B2 | 10/2011 | Smith et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,046 | B2 | 10/2011 | Smith et al. |
| 8,052,024 | B2 | 11/2011 | Viola et al. |
| 8,056,788 | B2 | 11/2011 | Mastri et al. |
| 8,056,789 | B1 | 11/2011 | White et al. |
| 8,061,576 | B2 | 11/2011 | Cappola |
| 8,061,577 | B2 | 11/2011 | Racenet et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,036 | B1 | 12/2011 | Knodel |
| 8,074,861 | B2 | 12/2011 | Ehrenfels et al. |
| 8,083,118 | B2 | 12/2011 | Milliman et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,092,493 | B2 | 1/2012 | Marczyk |
| 8,100,309 | B2 | 1/2012 | Marczyk |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,118,207 | B2 | 2/2012 | Racenet et al. |
| 8,123,100 | B2 | 2/2012 | Holsten et al. |
| 8,127,976 | B2 | 3/2012 | Scirica et al. |
| 8,136,712 | B2 | 3/2012 | Zingman |
| 8,152,041 | B2 | 4/2012 | Kostrzewski |
| 8,157,145 | B2 | 4/2012 | Shelton, IV et al. |
| 8,157,150 | B2 | 4/2012 | Viola et al. |
| 8,157,152 | B2 | 4/2012 | Holsten et al. |
| 8,181,839 | B2 | 5/2012 | Beetel |
| 8,186,555 | B2 | 5/2012 | Shelton, IV et al. |
| 8,186,556 | B2 | 5/2012 | Viola |
| 8,186,560 | B2 | 5/2012 | Hess et al. |
| 8,191,752 | B2 | 6/2012 | Scirica |
| 8,196,795 | B2 | 6/2012 | Moore et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,411 | B2 | 7/2012 | Yates et al. |
| 8,210,416 | B2 | 7/2012 | Milliman et al. |
| 8,220,688 | B2 | 7/2012 | Laurent et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,274 | B2 | 8/2012 | Cappola |
| 8,236,010 | B2 | 8/2012 | Shelton et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,256,656 | B2 | 9/2012 | Milliman et al. |
| 8,272,552 | B2 | 9/2012 | Holsten et al. |
| 8,272,554 | B2 | 9/2012 | Whitman et al. |
| 8,281,972 | B2 | 10/2012 | Wixey et al. |
| 8,281,973 | B2 | 10/2012 | Wenchell et al. |
| 8,286,846 | B2 | 10/2012 | Smith et al. |
| 8,292,146 | B2 | 10/2012 | Holsten et al. |
| 8,292,148 | B2 | 10/2012 | Viola |
| 8,292,151 | B2 | 10/2012 | Viola |
| 8,292,152 | B2 | 10/2012 | Milliman et al. |
| 8,292,153 | B2 | 10/2012 | Jankowski |
| 8,292,157 | B2 | 10/2012 | Smith et al. |
| 8,308,041 | B2 | 11/2012 | Kostrzewski |
| 8,308,043 | B2 | 11/2012 | Bindra et al. |
| 8,317,070 | B2 | 11/2012 | Hueil et al. |
| 8,322,455 | B2 | 12/2012 | Shelton, IV et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,348,125 | B2 | 1/2013 | Viola et al. |
| 8,348,129 | B2 | 1/2013 | Bedi et al. |

(56) References Cited

U.S. PATENT DOCUMENTS 8,348,131 B2 1/2013 Omaits et al.
8,353,440 B2 1/2013 Whitman et al.
8,360,297 B2 1/2013 Shelton, IV et al.
8,360,299 B2 1/2013 Zemlok et al.
8,393,513 B2 3/2013 Jankowski
8,397,972 B2 3/2013 Kostrzewski
8,397,973 B1 3/2013 Hausen
8,403,198 B2 3/2013 Sorrentino et al.
8,413,868 B2 4/2013 Cappola
8,414,577 B2 4/2013 Boudreaux et al.
8,418,906 B2 4/2013 Farascioni et al.
8,418,907 B2 4/2013 Johnson et al.
8,418,908 B1 4/2013 Beardsley
8,419,768 B2 4/2013 Marczyk
8,439,246 B1 5/2013 Knodel
8,444,036 B2 5/2013 Shelton, IV
8,453,907 B2 6/2013 Laurent et al.
8,453,912 B2 6/2013 Mastri et al.
8,453,913 B2 6/2013 Milliman
8,459,520 B2 6/2013 Giordano et al.
8,459,522 B2 6/2013 Marczyk
8,464,922 B2 6/2013 Marczyk
8,469,252 B2 6/2013 Holcomb et al.
8,479,967 B2 7/2013 Marczyk
8,496,152 B2 7/2013 Viola
8,496,155 B2 7/2013 Knodel
8,496,156 B2 7/2013 Sniffin et al.
8,496,683 B2 7/2013 Prommersberger et al.
8,505,799 B2 8/2013 Viola et al.
8,505,801 B2 8/2013 Ehrenfels et al.
8,517,239 B2 8/2013 Scheib et al.
8,517,240 B1 8/2013 Mata et al.
8,523,043 B2 9/2013 Ullrich et al.
8,540,130 B2 9/2013 Moore et al.
8,540,133 B2 9/2013 Bedi et al.
8,540,625 B2 9/2013 Miyoshi
8,544,712 B2 10/2013 Jankowski
8,556,151 B2 10/2013 Viola
8,556,152 B2 10/2013 Marczyk et al.
8,556,153 B1 10/2013 Knodel
8,561,871 B2 10/2013 Rajappa et al.
8,561,874 B2 10/2013 Scirica
8,573,459 B2 11/2013 Smith et al.
8,573,460 B2 11/2013 Cappola
8,573,462 B2 11/2013 Smith et al.
8,573,463 B2 11/2013 Scirica et al.
8,573,464 B2 11/2013 Nalagatla et al.
8,579,176 B2 11/2013 Smith et al.
8,579,177 B2 11/2013 Beetel
8,584,919 B2 11/2013 Hueil et al.
8,584,921 B2 11/2013 Scirica
8,596,513 B2 12/2013 Olson
8,608,043 B2 12/2013 Scirica
8,608,045 B2 12/2013 Smith et al.
8,616,427 B2 12/2013 Viola
8,622,274 B2 1/2014 Yates et al.
8,627,992 B2 1/2014 Edoga et al.
8,627,993 B2 1/2014 Smith et al.
8,627,995 B2 1/2014 Smith et al.
8,631,990 B1 1/2014 Park et al.
8,632,525 B2 1/2014 Kerr et al.
8,632,535 B2 1/2014 Shelton, IV et al.
8,636,189 B1 1/2014 Knodel et al.
8,636,190 B2 1/2014 Zemlok et al.
8,636,192 B2 1/2014 Farascioni et al.
8,636,193 B2 1/2014 Whitman et al.
8,636,762 B2 1/2014 Whitman et al.
8,636,766 B2 1/2014 Milliman et al.
8,657,174 B2 2/2014 Yates et al.
8,657,176 B2 2/2014 Shelton, IV et al.
8,657,178 B2 2/2014 Hueil et al.
8,672,209 B2 3/2014 Crainich
8,672,951 B2 3/2014 Smith et al.
8,685,004 B2 4/2014 Zemlock et al.
8,695,865 B2 4/2014 Smith et al.
8,696,665 B2 4/2014 Hunt et al.
8,708,211 B2 4/2014 Zemlok et al.
8,708,213 B2 4/2014 Shelton, IV et al.
8,740,034 B2 6/2014 Morgan et al.
8,740,035 B2 6/2014 Mastri et al.
8,740,036 B2 6/2014 Williams
8,752,748 B2 6/2014 Whitman et al.
8,763,876 B2 7/2014 Kostrzewski
8,770,458 B2 7/2014 Scirica
8,770,459 B2 7/2014 Racenet et al.
8,789,741 B2 7/2014 Baxter, III et al.
8,800,839 B2 8/2014 Beetel
8,800,840 B2 8/2014 Jankowski
8,800,841 B2 8/2014 Ellerhorst et al.
8,806,973 B2 8/2014 Ross et al.
8,807,414 B2 8/2014 Ross et al.
8,820,603 B2 9/2014 Shelton, IV et al.
8,820,608 B2 9/2014 Miyamoto
8,833,631 B2 9/2014 Munro, III et al.
8,840,003 B2 9/2014 Morgan et al.
8,858,571 B2 10/2014 Shelton, IV et al.
8,875,971 B2 11/2014 Hall et al.
8,875,972 B2 11/2014 Weisenburgh, II et al.
8,887,979 B2 11/2014 Mastri et al.
8,899,462 B2 12/2014 Kostrzewski et al.
8,899,463 B2 12/2014 Schall et al.
8,905,288 B2 12/2014 Wenchell
8,920,435 B2 12/2014 Smith et al.
8,925,783 B2 1/2015 Zemlok et al.
8,931,679 B2 1/2015 Kostrzewski
8,931,683 B2 1/2015 Racenet et al.
8,939,343 B2 1/2015 Milliman et al.
8,967,444 B2 3/2015 Beetel
8,967,446 B2 3/2015 Beardsley et al.
8,967,447 B2 3/2015 Hartoumbekis
8,968,276 B2 3/2015 Zemlok et al.
8,973,803 B2 3/2015 Hall et al.
8,979,827 B2 3/2015 Cappola
9,004,340 B2 4/2015 Scirica
9,010,611 B2 4/2015 Ross et al.
9,016,541 B2 4/2015 Viola et al.
9,016,545 B2 4/2015 Aranyi et al.
9,022,271 B2 5/2015 Scirica
9,023,014 B2 5/2015 Chowaniec et al.
9,027,817 B2 5/2015 Milliman et al.
9,027,818 B2 5/2015 Scirica et al.
9,033,202 B2 5/2015 Scirica
9,038,880 B1 5/2015 Donohoe
9,055,943 B2 6/2015 Zemlok et al.
9,072,515 B2 7/2015 Hall et al.
9,084,601 B2 7/2015 Moore et al.
9,101,358 B2 8/2015 Kerr et al.
9,204,876 B2 12/2015 Cappola et al.
9,237,890 B2 1/2016 Kostrzewski
9,265,585 B2 2/2016 Wingardner et al.
9,282,966 B2 3/2016 Shelton, IV et al.
9,386,984 B2 7/2016 Aronhalt et al.
9,402,629 B2 8/2016 Ehrenfels et al.
9,510,830 B2 12/2016 Shelton, IV et al.
9,532,782 B2 1/2017 Kostrzewski
9,662,108 B2 5/2017 Williams
9,737,302 B2 8/2017 Shelton, IV et al.
9,737,303 B2 8/2017 Shelton, IV et al.
9,797,486 B2 10/2017 Zergiebel et al.
2002/0025243 A1 2/2002 Heck
2002/0029044 A1 3/2002 Monassevitch et al.
2002/0062136 A1 5/2002 Hillstead
2002/0120279 A1 8/2002 Deguillebon et al.
2003/0130677 A1 7/2003 Whitman et al.
2004/0006372 A1 1/2004 Racenet et al.
2004/0138705 A1 7/2004 Heino et al.
2005/0234478 A1 10/2005 Wixey
2006/0097026 A1 5/2006 Shelton, IV
2006/0100644 A1 5/2006 Viola
2006/0180634 A1 8/2006 Shelton, IV et al.
2006/0235442 A1 10/2006 Huitema
2006/0289602 A1 12/2006 Wales et al.
2007/0034664 A1 2/2007 Jiang
2007/0039997 A1 2/2007 Mather et al.

(56) References Cited

U.S. PATENT DOCUMENTS

| | | | | |
|---|---|---|---|---|
| 2007/0057014 | A1 | 3/2007 | Whitman et al. | |
| 2007/0068990 | A1 | 3/2007 | Shelton, IV | |
| 2007/0084897 | A1 | 4/2007 | Shelton, IV et al. | |
| 2007/0102472 | A1 | 5/2007 | Shelton, IV | |
| 2007/0119901 | A1 | 5/2007 | Ehrenfels et al. | |
| 2007/0131732 | A1 | 6/2007 | Holsten et al. | |
| 2007/0175950 | A1 | 8/2007 | Shelton, IV et al. | |
| 2007/0175951 | A1 | 8/2007 | Shelton, IV et al. | |
| 2008/0029574 | A1 | 2/2008 | Shelton et al. | |
| 2008/0029575 | A1 | 2/2008 | Shelton et al. | |
| 2008/0041918 | A1 | 2/2008 | Holsten et al. | |
| 2008/0078807 | A1 | 4/2008 | Hess et al. | |
| 2008/0083807 | A1 | 4/2008 | Beardsley et al. | |
| 2008/0169333 | A1 | 7/2008 | Shelton et al. | |
| 2008/0179375 | A1 | 7/2008 | Scirica | |
| 2008/0255607 | A1 | 10/2008 | Zemick | |
| 2009/0001129 | A1 | 1/2009 | Marczyk | |
| 2009/0001130 | A1 | 1/2009 | Hess et al. | |
| 2009/0026245 | A1 | 1/2009 | Holsten et al. | |
| 2009/0048589 | A1 | 2/2009 | Takashino et al. | |
| 2009/0057369 | A1 | 3/2009 | Smith et al. | |
| 2009/0090763 | A1 | 4/2009 | Zemlok et al. | |
| 2009/0145947 | A1* | 6/2009 | Scirica ............... | A61B 17/0686 227/176.1 |
| 2009/0198272 | A1 | 8/2009 | Kerver et al. | |
| 2009/0206131 | A1 | 8/2009 | Weisenburgh, II et al. | |
| 2009/0206133 | A1 | 8/2009 | Morgan et al. | |
| 2009/0206137 | A1 | 8/2009 | Hall et al. | |
| 2009/0277948 | A1 | 11/2009 | Beardsley et al. | |
| 2009/0277949 | A1 | 11/2009 | Viola et al. | |
| 2010/0069942 | A1 | 3/2010 | Shelton, IV | |
| 2010/0072258 | A1 | 3/2010 | Farascioni et al. | |
| 2010/0089970 | A1 | 4/2010 | Smith et al. | |
| 2010/0193566 | A1 | 8/2010 | Scheib et al. | |
| 2010/0230465 | A1 | 9/2010 | Smith et al. | |
| 2010/0331820 | A1 | 12/2010 | Prisco et al. | |
| 2011/0036892 | A1 | 2/2011 | Marczyk et al. | |
| 2011/0042440 | A1 | 2/2011 | Holsten et al. | |
| 2011/0087276 | A1 | 4/2011 | Bedi et al. | |
| 2011/0108601 | A1 | 5/2011 | Clark et al. | |
| 2011/0108603 | A1 | 5/2011 | Racenet et al. | |
| 2011/0121049 | A1 | 5/2011 | Malinouskas et al. | |
| 2011/0125138 | A1 | 5/2011 | Malinouskas et al. | |
| 2011/0127185 | A1 | 6/2011 | Ward | |
| 2011/0139852 | A1 | 6/2011 | Zingman | |
| 2011/0147433 | A1 | 6/2011 | Shelton, IV et al. | |
| 2011/0155784 | A1 | 6/2011 | Shelton, IV et al. | |
| 2011/0155787 | A1 | 6/2011 | Baxter, III et al. | |
| 2011/0290851 | A1 | 12/2011 | Shelton, IV et al. | |
| 2011/0290853 | A1 | 12/2011 | Shelton, IV et al. | |
| 2012/0061446 | A1 | 3/2012 | Knodel et al. | |
| 2012/0074198 | A1 | 3/2012 | Hultema et al. | |
| 2012/0074200 | A1 | 3/2012 | Schmid et al. | |
| 2012/0078243 | A1 | 3/2012 | Worrell et al. | |
| 2012/0080482 | A1 | 4/2012 | Schall et al. | |
| 2012/0080498 | A1 | 4/2012 | Shelton, IV et al. | |
| 2012/0091182 | A1 | 4/2012 | Marczyk | |
| 2012/0109186 | A1 | 5/2012 | Parrott et al. | |
| 2012/0168487 | A1 | 7/2012 | Holsten et al. | |
| 2012/0193396 | A1 | 8/2012 | Zemlok et al. | |
| 2012/0211542 | A1 | 8/2012 | Racenet | |
| 2012/0253298 | A1 | 10/2012 | Henderson et al. | |
| 2012/0286022 | A1 | 11/2012 | Olson et al. | |
| 2012/0318844 | A1 | 12/2012 | Shelton, IV et al. | |
| 2012/0325893 | A1 | 12/2012 | Pastorelli et al. | |
| 2013/0012701 | A1 | 1/2013 | Kostrzewski | |
| 2013/0015229 | A1 | 1/2013 | Viola | |
| 2013/0015230 | A1 | 1/2013 | Wixey | |
| 2013/0015232 | A1 | 1/2013 | Smith et al. | |
| 2013/0015233 | A1 | 1/2013 | Viola | |
| 2013/0020375 | A1 | 1/2013 | Shelton, IV et al. | |
| 2013/0037595 | A1 | 2/2013 | Gupta et al. | |
| 2013/0048697 | A1 | 2/2013 | Shelton, IV et al. | |
| 2013/0056521 | A1 | 3/2013 | Swensgard | |
| 2013/0079814 | A1 | 3/2013 | Hess et al. | |
| 2013/0087603 | A1 | 4/2013 | Viola | |
| 2013/0092717 | A1 | 4/2013 | Marczyk et al. | |
| 2013/0098964 | A1 | 4/2013 | Smith et al. | |
| 2013/0098965 | A1 | 4/2013 | Kostrzewski et al. | |
| 2013/0098969 | A1 | 4/2013 | Scirica et al. | |
| 2013/0105545 | A1 | 5/2013 | Burbank | |
| 2013/0105547 | A1 | 5/2013 | Beardsley | |
| 2013/0105548 | A1 | 5/2013 | Hodgkinson et al. | |
| 2013/0105549 | A1 | 5/2013 | Holsten et al. | |
| 2013/0112730 | A1 | 5/2013 | Whitman et al. | |
| 2013/0112731 | A1 | 5/2013 | Hodgkinson | |
| 2013/0126583 | A1 | 5/2013 | Hueil et al. | |
| 2013/0126586 | A1 | 5/2013 | Zhang et al. | |
| 2013/0146640 | A1 | 6/2013 | Jankowski | |
| 2013/0172928 | A1 | 7/2013 | Kostrzewski | |
| 2013/0172929 | A1 | 7/2013 | Hess et al. | |
| 2013/0175317 | A1 | 7/2013 | Yates et al. | |
| 2013/0175322 | A1 | 7/2013 | Yates et al. | |
| 2013/0184718 | A1 | 7/2013 | Smith et al. | |
| 2013/0186931 | A1 | 7/2013 | Beardsley | |
| 2013/0186932 | A1 | 7/2013 | Shelton, IV et al. | |
| 2013/0186933 | A1 | 7/2013 | Shelton, IV et al. | |
| 2013/0193188 | A1 | 8/2013 | Shelton, IV et al. | |
| 2013/0200132 | A1 | 8/2013 | Moore et al. | |
| 2013/0206816 | A1 | 8/2013 | Penna | |
| 2013/0214025 | A1 | 8/2013 | Zemlok et al. | |
| 2013/0221065 | A1 | 8/2013 | Aronhalt et al. | |
| 2013/0240604 | A1 | 9/2013 | Knodel | |
| 2013/0248582 | A1 | 9/2013 | Scirica | |
| 2013/0256370 | A1 | 10/2013 | Smith et al. | |
| 2013/0256371 | A1 | 10/2013 | Shelton, IV | |
| 2013/0270321 | A1 | 10/2013 | Marczyk | |
| 2013/0270323 | A1 | 10/2013 | Marczyk | |
| 2013/0284789 | A1 | 10/2013 | Smith et al. | |
| 2013/0284791 | A1 | 10/2013 | Olson et al. | |
| 2013/0299552 | A1 | 11/2013 | Viola | |
| 2013/0306702 | A1 | 11/2013 | Viola et al. | |
| 2013/0306703 | A1 | 11/2013 | Ehrenfels et al. | |
| 2013/0306706 | A1 | 11/2013 | Knodel | |
| 2013/0313303 | A1 | 11/2013 | Shelton, IV et al. | |
| 2013/0327809 | A1 | 12/2013 | Shelton, IV et al. | |
| 2013/0327810 | A1 | 12/2013 | Swayze et al. | |
| 2013/0334278 | A1 | 12/2013 | Kerr et al. | |
| 2013/0334280 | A1 | 12/2013 | Krehel et al. | |
| 2013/0334281 | A1 | 12/2013 | Williams | |
| 2013/0334283 | A1 | 12/2013 | Swayze et al. | |
| 2013/0334284 | A1 | 12/2013 | Swayze et al. | |
| 2013/0334285 | A1 | 12/2013 | Swayze et al. | |
| 2013/0334286 | A1 | 12/2013 | Swayze et al. | |
| 2013/0334287 | A1 | 12/2013 | Shelton, IV | |
| 2013/0334288 | A1 | 12/2013 | Shelton, IV | |
| 2014/0014704 | A1 | 1/2014 | Onukuri et al. | |
| 2014/0014707 | A1 | 1/2014 | Onukuri et al. | |
| 2014/0021239 | A1 | 1/2014 | Kostrzewski | |
| 2014/0025046 | A1 | 1/2014 | Williams et al. | |
| 2014/0027491 | A1 | 1/2014 | Beardsley et al. | |
| 2014/0027493 | A1 | 1/2014 | Jankowski | |
| 2014/0042204 | A1 | 2/2014 | Beetel | |
| 2014/0103092 | A1 | 4/2014 | Kostrzewski et al. | |
| 2014/0103093 | A1 | 4/2014 | Koch, Jr. et al. | |
| 2014/0107640 | A1 | 4/2014 | Yates et al. | |
| 2014/0110453 | A1 | 4/2014 | Wingardner et al. | |
| 2014/0131416 | A1 | 5/2014 | Whitman et al. | |
| 2014/0135832 | A1 | 5/2014 | Park et al. | |
| 2014/0151433 | A1 | 6/2014 | Shelton, IV et al. | |
| 2014/0151434 | A1 | 6/2014 | Shelton, IV et al. | |
| 2014/0158746 | A1 | 6/2014 | Mastri et al. | |
| 2014/0166727 | A1 | 6/2014 | Swayze et al. | |
| 2014/0175146 | A1 | 6/2014 | Knodel | |
| 2014/0175149 | A1 | 6/2014 | Smith et al. | |
| 2014/0203063 | A1 | 7/2014 | Hessler et al. | |
| 2014/0205637 | A1 | 7/2014 | Widenhouse et al. | |
| 2014/0224856 | A1 | 8/2014 | Smith et al. | |
| 2014/0236173 | A1 | 8/2014 | Scirica et al. | |
| 2014/0236184 | A1 | 8/2014 | Leimbach | |
| 2014/0239038 | A1 | 8/2014 | Leimbach et al. | |
| 2014/0239041 | A1 | 8/2014 | Zerkle et al. | |
| 2014/0239044 | A1 | 8/2014 | Hoffman | |
| 2014/0246474 | A1 | 9/2014 | Hall et al. | |

(56) References Cited

U.S. PATENT DOCUMENTS

| | | | |
|---|---|---|---|
| 2014/0246475 | A1 | 9/2014 | Hall et al. |
| 2014/0246478 | A1 | 9/2014 | Baber et al. |
| 2014/0246479 | A1 | 9/2014 | Baber et al. |
| 2014/0260746 | A1 | 9/2014 | Sakaguchi et al. |
| 2014/0263537 | A1 | 9/2014 | Leimbach et al. |
| 2014/0263539 | A1 | 9/2014 | Leimbach et al. |
| 2014/0263541 | A1 | 9/2014 | Leimbach et al. |
| 2014/0263542 | A1 | 9/2014 | Leimbach et al. |
| 2014/0263543 | A1 | 9/2014 | Leimbach et al. |
| 2014/0263545 | A1 | 9/2014 | Williams et al. |
| 2014/0263546 | A1 | 9/2014 | Aranyi |
| 2014/0263550 | A1 | 9/2014 | Aranyi et al. |
| 2014/0263553 | A1 | 9/2014 | Leimbach et al. |
| 2014/0263554 | A1 | 9/2014 | Leimbach et al. |
| 2014/0263555 | A1 | 9/2014 | Hufnagel et al. |
| 2014/0263559 | A1 | 9/2014 | Williams et al. |
| 2014/0263562 | A1 | 9/2014 | Patel et al. |
| 2014/0263564 | A1 | 9/2014 | Leimbach et al. |
| 2014/0263565 | A1 | 9/2014 | Lytle, IV et al. |
| 2014/0263566 | A1 | 9/2014 | Williams et al. |
| 2014/0263567 | A1 | 9/2014 | Williams et al. |
| 2014/0263568 | A1 | 9/2014 | Williams et al. |
| 2014/0263569 | A1 | 9/2014 | Williams et al. |
| 2014/0263570 | A1 | 9/2014 | Hopkins et al. |
| 2014/0263571 | A1 | 9/2014 | Morgan et al. |
| 2014/0263572 | A1 | 9/2014 | Shelton, IV et al. |
| 2014/0284372 | A1 | 9/2014 | Kostrzewski |
| 2014/0291378 | A1 | 10/2014 | Shelton, IV et al. |
| 2014/0299649 | A1 | 10/2014 | Shelton, IV et al. |
| 2014/0305986 | A1 | 10/2014 | Hall et al. |
| 2014/0305988 | A1 | 10/2014 | Boudreaux et al. |
| 2014/0305992 | A1 | 10/2014 | Kimsey et al. |
| 2014/0305994 | A1 | 10/2014 | Parihar et al. |
| 2014/0353359 | A1 | 12/2014 | Hall et al. |
| 2015/0008248 | A1 | 1/2015 | Giordano et al. |
| 2015/0034697 | A1 | 2/2015 | Mastri et al. |
| 2015/0041518 | A1 | 2/2015 | Shelton, IV et al. |
| 2015/0053738 | A1 | 2/2015 | Morgan et al. |
| 2015/0053740 | A1 | 2/2015 | Shelton, IV |
| 2015/0053741 | A1 | 2/2015 | Shelton, IV et al. |
| 2015/0053742 | A1 | 2/2015 | Shelton, IV et al. |
| 2015/0053743 | A1 | 2/2015 | Yates et al. |
| 2015/0053744 | A1 | 2/2015 | Swayze et al. |
| 2015/0053745 | A1 | 2/2015 | Yates et al. |
| 2015/0053746 | A1 | 2/2015 | Shelton, IV et al. |
| 2015/0053748 | A1 | 2/2015 | Yates et al. |
| 2015/0053749 | A1 | 2/2015 | Shelton, IV et al. |
| 2015/0054753 | A1 | 2/2015 | Morgan et al. |
| 2015/0060516 | A1 | 3/2015 | Collings et al. |
| 2015/0060517 | A1 | 3/2015 | Williams |
| 2015/0060521 | A1 | 3/2015 | Weisenburgh, II et al. |
| 2015/0076205 | A1 | 3/2015 | Zergiebel |
| 2015/0076206 | A1 | 3/2015 | Sapre |
| 2015/0076209 | A1 | 3/2015 | Shelton, IV et al. |
| 2015/0076210 | A1 | 3/2015 | Shelton, IV et al. |
| 2015/0076212 | A1 | 3/2015 | Shelton, IV |
| 2015/0083781 | A1 | 3/2015 | Giordano et al. |
| 2015/0083783 | A1 | 3/2015 | Shelton, IV et al. |
| 2015/0090760 | A1 | 4/2015 | Giordano et al. |
| 2015/0090761 | A1 | 4/2015 | Giordano et al. |
| 2015/0090762 | A1 | 4/2015 | Giordano et al. |
| 2015/0090764 | A1 | 4/2015 | Zemlok et al. |
| 2015/0108201 | A1 | 4/2015 | Williams |
| 2015/0122872 | A1 | 5/2015 | Olson et al. |
| 2015/0127046 | A1 | 5/2015 | Peterson |
| 2015/0129631 | A1 | 5/2015 | Beetel |
| 2015/0129634 | A1 | 5/2015 | Shelton, IV et al. |
| 2015/0133995 | A1 | 5/2015 | Shelton, IV et al. |
| 2015/0133996 | A1 | 5/2015 | Shelton, IV et al. |
| 2015/0134076 | A1 | 5/2015 | Shelton, IV et al. |
| 2015/0144678 | A1 | 5/2015 | Hall et al. |
| 2015/0201935 | A1 | 7/2015 | Weisenburgh, II et al. |
| 2015/0208902 | A1 | 7/2015 | Okamoto |
| 2015/0245834 | A1 | 9/2015 | Scirica et al. |
| 2015/0272576 | A1 | 10/2015 | Cappola |
| 2015/0289873 | A1 | 10/2015 | Shelton, IV et al. |
| 2015/0297221 | A1 | 10/2015 | Kerr et al. |
| 2015/0297233 | A1 | 10/2015 | Huitema et al. |
| 2015/0380187 | A1 | 12/2015 | Zergiebel et al. |
| 2016/0000439 | A1 | 1/2016 | Weisenburgh, II et al. |
| 2016/0000440 | A1 | 1/2016 | Weisenburgh et al. |
| 2016/0058447 | A1 | 3/2016 | Posada et al. |
| 2016/0183948 | A1 | 6/2016 | Shelton, IV et al. |
| 2016/0338702 | A1 | 11/2016 | Ehrenfels et al. |
| 2016/0374672 | A1 | 12/2016 | Bear et al. |
| 2016/0374675 | A1 | 12/2016 | Shelton, IV et al. |
| 2017/0007241 | A1 | 1/2017 | Shelton, IV et al. |
| 2017/0007242 | A1 | 1/2017 | Shelton, IV et al. |
| 2017/0007243 | A1 | 1/2017 | Shelton, IV et al. |
| 2017/0007249 | A1 | 1/2017 | Shelton, IV et al. |
| 2017/0231633 | A1 | 8/2017 | Marczyk et al. |
| 2017/0245856 | A1 | 8/2017 | Baxter, III et al. |
| 2017/0245858 | A1 | 8/2017 | Williams |
| 2017/0281161 | A1 | 10/2017 | Shelton, IV et al. |
| 2017/0281165 | A1 | 10/2017 | Harris et al. |
| 2017/0281168 | A1 | 10/2017 | Shelton, IV et al. |
| 2017/0290583 | A1 | 10/2017 | Reed et al. |
| 2017/0290584 | A1 | 10/2017 | Jasemian et al. |

FOREIGN PATENT DOCUMENTS

| | | | |
|---|---|---|---|
| EP | 0 514 139 | A2 | 11/1992 |
| EP | 0 536 903 | A2 | 4/1993 |
| EP | 0 596 543 | A1 | 5/1994 |
| EP | 1 523 944 | A1 | 4/2005 |
| EP | 1 759 812 | A1 | 3/2007 |
| EP | 1 915 953 | A1 | 4/2008 |
| EP | 1 479 348 | B1 | 7/2008 |
| EP | 2 044 893 | A2 | 9/2008 |
| EP | 2 005 902 | A2 | 12/2008 |
| EP | 2 090 241 | A1 | 8/2009 |
| EP | 2 263 568 | A2 | 12/2010 |
| EP | 2 361 562 | A1 | 8/2011 |
| EP | 2 462 875 | A2 | 6/2012 |
| EP | 2 486 859 | A2 | 8/2012 |
| EP | 2 764 833 | A2 | 8/2014 |
| EP | 2 772 192 | A1 | 9/2014 |
| EP | 2 777 530 | A1 | 9/2014 |
| EP | 2 815 705 | A1 | 12/2014 |
| EP | 2 923 661 | A2 | 3/2015 |
| EP | 2 853 204 | A1 | 4/2015 |
| EP | 2 891 462 | A1 | 7/2015 |
| EP | 2 926 742 | A1 | 10/2015 |
| EP | 2 942 020 | A2 | 11/2015 |
| EP | 2 959 851 | A1 | 12/2015 |
| EP | 3 135 225 | A2 | 3/2017 |
| EP | 3 238 639 | A2 | 3/2017 |
| EP | 3 338 653 | A1 | 6/2018 |
| EP | 3 338 698 | A1 | 6/2018 |
| EP | 3 338 702 | A1 | 6/2018 |
| JP | 2001-087272 | A | 4/2001 |
| RU | 2063710 | | 7/1996 |
| WO | WO 83/02247 | A1 | 7/1983 |
| WO | WO 94/24947 | A1 | 11/1994 |
| WO | WO 02/30296 | A2 | 4/2002 |
| WO | WO 02/096327 | A2 | 12/2002 |
| WO | WO 2003/094747 | A1 | 11/2003 |
| WO | WO 2004/032762 | A1 | 4/2004 |
| WO | WO 2012/052729 | A1 | 4/2012 |
| WO | WO 2014/139440 | A1 | 9/2014 |

OTHER PUBLICATIONS

Justright Surgical, JustRight Surgery, Dec. 31, 2014.

International Searching Authority/US, The International Search Report and the Written Opinion of the International Searching Authority for International Application No. PCT/US2014/028811, titled Surgical Stapler Having Actuation Mechanism with Rotatable Shaft, mailed Aug. 5, 2014.

The International Bureau of WIPO, International Preliminary Report on Patentability, dated Sep. 15, 2015, for International Application No. PCT/US2014/028811.

(56) References Cited

OTHER PUBLICATIONS

European Patent Office, European Search Report for European Application No. EP 14764812.5, entitled "Surgical Stapler Having Actuation Mechanism With Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ Epo, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ Epo, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," mailed Sep. 12, 2017, 22 pgs.
European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.
European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, European Search Report for European Application No. 07784007.2, entitled "Surgical Stapler," dated Jun. 15, 2012, 6 pgs.
International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.
European Patent Office, International Search Report and Written Opinion for International Application No. PCT/US2014/028211, entitled "Surgical Stapler with Partial Pockets," mailed Sep. 8, 2014, 17 pgs.
International Searching Authority, U.S., The International Search Report and the Written Opinion of the International Searching authority for international application PCT/US2015/0035379, titled "Surgical Stapler with Circumferential Firing", mailed Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, Partial European Search Report for European Application No. EP 14762896.0, entitled "Surgical Stapler with Expandable Jaw," dated Apr. 10, 2017, 6 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, Extended European Search Report for European ApplicationNo. EP 20157713.7, entitled "Surgical Stapler with Expandable Jaw," dated May 11, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," mailed Aug. 13, 2020, 20 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, for International Application No. PCT/US2021/057231, entitled "Material Combinations and Processing Methods for a Surgical Instrument," dated May 11, 2023, 10 pgs.
The International Bureau of WIPO, International Preliminary Report on Patentability, for International Application No. PCT/US2021/

(56) References Cited

OTHER PUBLICATIONS 057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.
European Patent Office, Partial Extended European Search Report for European Patent Application No. 23198488.1, titled "Surgical Stapler with Self-Adjusting Staple Height," dated Jan. 23, 2024, 8 pgs.

* cited by examiner

SURGICAL STAPLER HANDLE ASSEMBLY HAVING ACTUATION MECHANISM WITH LONGITUDINALLY ROTATABLE SHAFT

CROSS REFERENCE TO RELATED APPLICATIONS

This application is a continuation of U.S. patent application Ser. No. 18/494,610 entitled "SURGICAL STAPLER HANDLE ASSEMBLY HAVING ACTUATION MECHANISM WITH LONGITUDINALLY ROTATABLE SHAFT" filed on Oct. 25, 2023, which is a continuation of U.S. patent application Ser. No. 17/980,395 entitled "SURGICAL STAPLER HANDLE ASSEMBLY HAVING ACTUATION MECHANISM WITH LONGITUDINALLY ROTATABLE SHAFT" filed on Nov. 3, 2022, which is now U.S. Pat. No. 11,844,491, which is a continuation of U.S. patent application Ser. No. 17/141,050 entitled "SURGICAL STAPLER HANDLE ASSEMBLY HAVING ACTUATION MECHANISM WITH LONGITUDINALLY ROTATABLE SHAFT" filed on Jan. 4, 2021, which is now U.S. Pat. No. 11,529,141, which is a continuation of U.S. patent application Ser. No. 16/789,152 entitled "SURGICAL STAPLER HANDLE ASSEMBLY HAVING ACTUATION MECHANISM WITH LONGITUDINALLY ROTATABLE SHAFT" filed on Feb. 12, 2020, which is now U.S. Pat. No. 10,912,565, which is a continuation of U.S. patent application Ser. No. 15/598,458 entitled "SURGICAL STAPLER HANDLE ASSEMBLY HAVING ACTUATION MECHANISM WITH LONGITUDINALLY ROTATABLE SHAFT" filed on May 18, 2017, which is now U.S. Pat. No. 10,595,866, which is a continuation of U.S. patent application Ser. No. 14/213,493 entitled "SURGICAL STAPLER HANDLE ASSEMBLY HAVING ACTUATION MECHANISM WITH LONGITUDINALLY ROTATABLE SHAFT" filed on Mar. 14, 2014, which is now U.S. Pat. No. 9,668,732, which claims priority to and benefit of U.S. Provisional Patent Application Ser. No. 61/794,700, entitled "SURGICAL STAPLER HAVING ACTUATION MECHANISM WITH ROTATABLE SHAFT," filed on Mar. 15, 2013. The entireties of these prior applications are hereby incorporated herein by reference.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a jaw assembly, and a handle assembly. The elongate shaft has a proximal end and a distal end. The elongate shaft defines a longitudinal axis between the proximal end and the distal end. The jaw assembly is positioned at the distal end of the elongate shaft. The jaw assembly comprises a first jaw, a second jaw, and a plurality of staples. The jaw assembly is selectively positionable in one of a closed configuration, an open configuration, and a firing configuration. The handle assembly is positioned at the proximal end of the elongate shaft. The handle assembly comprises a stationary handle, a movable trigger pivotably coupled to the stationary handle, and an actuation shaft. The actuation shaft is longitudinally slidable within the handle assembly with respect to the longitudinal axis of the actuation shaft and rotatable within the handle assembly with respect to the longitudinal axis. The actuation shaft is operably coupled to the jaw assembly and the actuation shaft is longitudinally slidable in a first direction from a first position corresponding to the open configuration of the jaw assembly to a second position corresponding to the closed configuration of the jaw assembly and from the second position to a third position corresponding to the firing configuration. The actuation shaft is operably coupled to the movable trigger. The actuation shaft is rotatable between a first orientation in which movement of the trigger moves the actuation shaft between the second position and the third position and a second orientation in which movement of the trigger moves the actuation shaft from the third position to the first position.

In certain embodiments, a handle assembly for a surgical stapler is provided. The surgical stapler comprises an elongate shaft having a proximal end and a distal end, the elongate shaft defining a longitudinal axis between the proximal end and the distal end, and a jaw assembly disposed at the distal end of the elongate shaft. The handle assembly comprises a housing, a stationary handle disposed on the housing, a movable handle, an actuation mechanism, and a coupler. The movable handle is pivotably coupled to the housing and pivotable between an open position spaced apart from the stationary handle and a closed position adjacent the stationary handle. The actuation mechanism comprises an advancing driver, a reversing driver, and an actuation shaft. The advancing driver is operably coupled to the movable handle and translatable distally with respect to the longitudinal axis responsive to movement of the movable handle from the open position to the closed position. The reversing driver is operably coupled to the movable handle and translatable proximally with respect to the longitudinal axis responsive to movement of the movable handle from the open position to the closed position. The actuation shaft extends along the longitudinal axis. The actuation shaft is rotatably coupled to the housing with respect to the longitudinal axis. The actuation shaft comprises an advancing surface and a reversing surface. The advancing surface extends longitudinally along the actuation shaft. The reversing surface extends longitudinally along the actuation shaft. The reversing surface is angularly offset from the advancing surface. The actuation shaft is rotatable between a first orientation in which the advancing driver engages the advancing surface and a second orientation in which the reversing driver engages the reversing surface. The coupler is adapted to engage the elongate shaft of the surgical stapler.

In certain embodiments, a handle assembly for a surgical stapler is provided. The handle assembly comprises a housing, a trigger pivotably coupled to the housing, and an actuation mechanism. The actuation mechanism comprises a forward driver, a reverse driver, an actuation shaft, and a selector. The forward driver is operably coupled to the trigger. The reverse driver is operably coupled to the trigger. The actuation shaft has a longitudinal axis. The actuation shaft is rotatably coupled to the housing relative to the longitudinal axis. The actuation shaft comprises a forward interface surface and a reverse interface surface angularly offset from the forward interface surface. The actuation shaft is rotatable between a first orientation in which the forward interface surface engages the forward driver to move the actuation shaft in a first direction responsive to pivotal movement of the trigger and a second orientation in which the reverse interface surface engages the reverse driver to move the actuation shaft in a second direction opposite the first direction responsive to pivotal movement of the trigger. The selector is operably coupled to the actuation shaft to selectively rotate the actuation shaft between the first orientation and the second orientation.

DETAILED DESCRIPTION OF THE INVENTION

Figure 1:
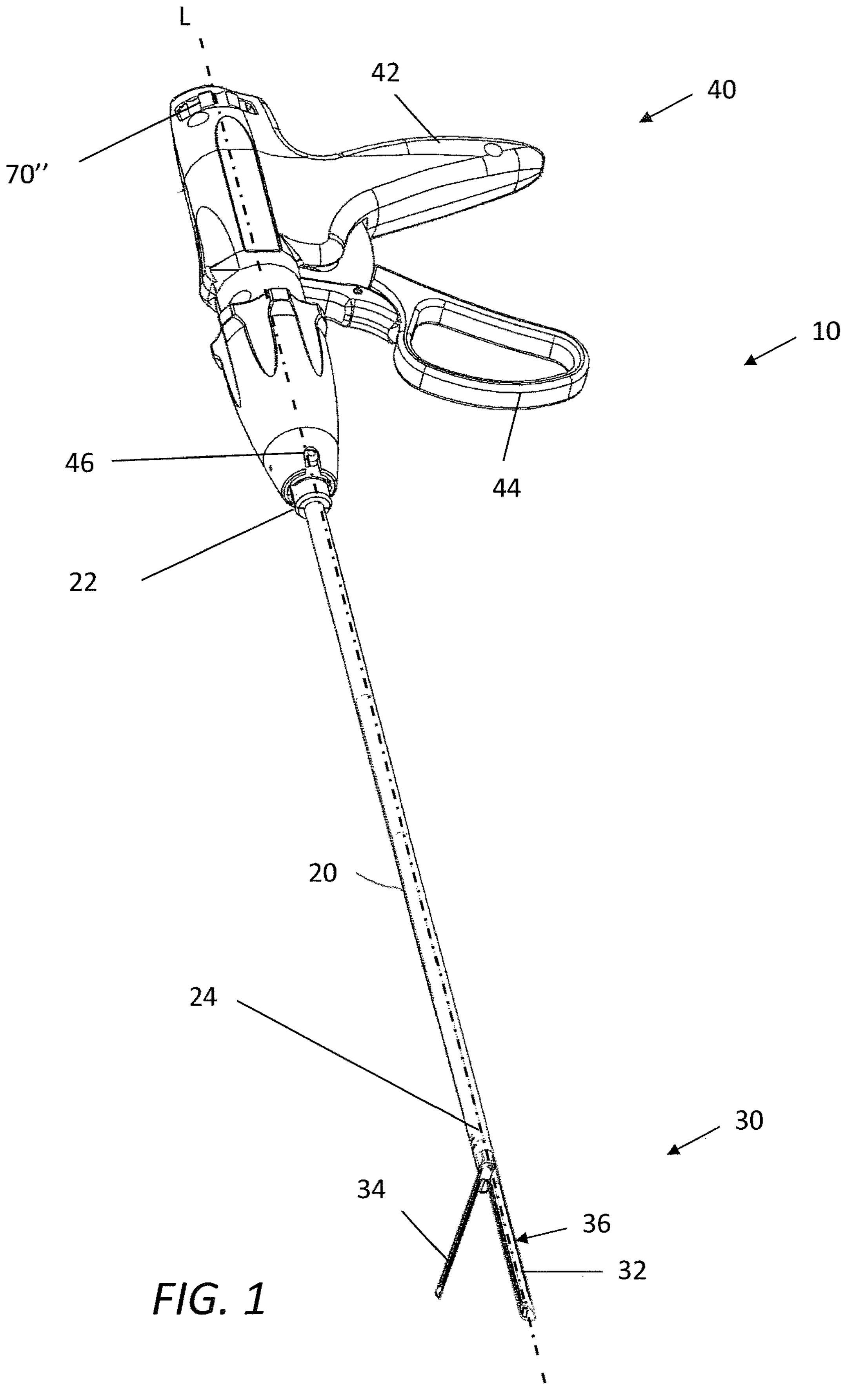
FIG. 1 is a perspective view of an embodiment of surgical stapling device with the jaws in an open configuration.
Figure 2:
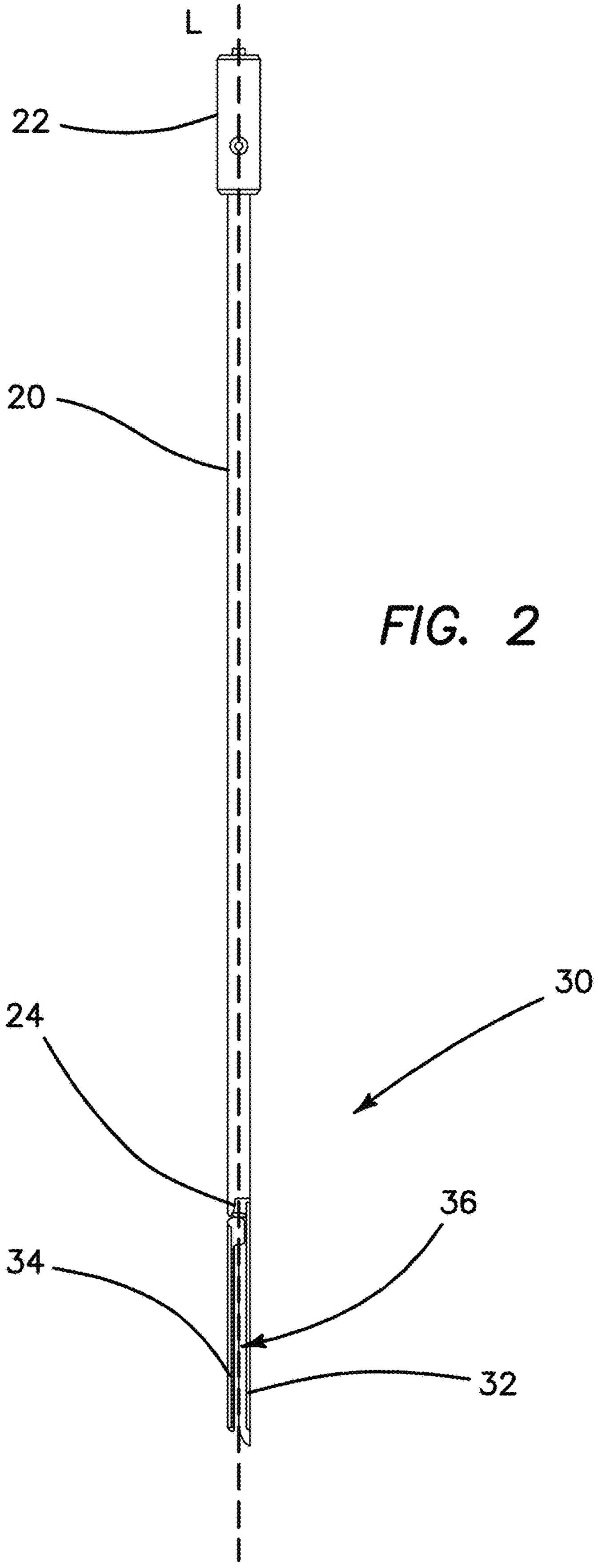
FIG. 2 is a perspective view of an embodiment of a cartridge for the surgical stapling device of FIG. 1 with the jaws in a closed configuration.

With reference to FIGS. 1-2, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. FIG. 2 illustrates a removable cartridge comprising the elongate shaft 20 and jaw assembly 30 of the surgical stapler 10 with the jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. Elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and remains stationary with respect to the elongate shaft 20. In other embodiments, it is contemplated that the jaw assembly 30 is articulable with respect to the elongate shaft 20. In an initial configuration, the first jaw 32 includes a plurality of staples 36 disposed therein.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIGS. 1 and 2, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configuration such as, for example, scissors-grip configurations, or in-line configurations. As further described in greater detail below, the handle assembly 40 houses an actuation mechanism configured to selectively advance an actuation shaft responsive to movement of the movable handle 44.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reasonable.

Figure 3:
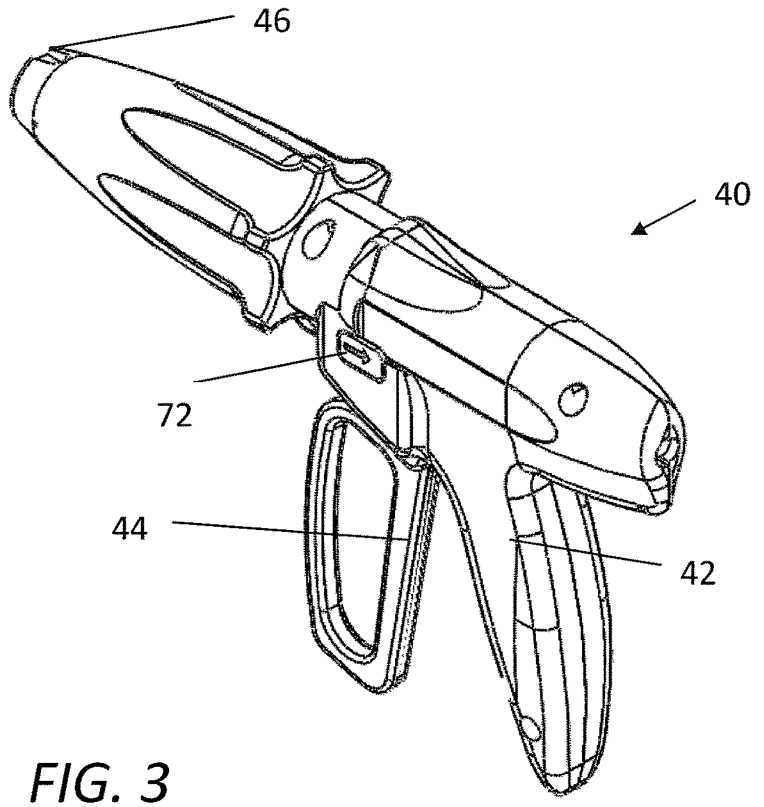
FIG. 3 is a perspective view of an embodiment of handle assembly for a surgical stapling device.

FIGS. 3-7 illustrate various views of an embodiment of handle assembly 40 for a surgical stapler 10. In FIG. 3, a perspective view of the handle assembly 40 as illustrated with the movable handle 44 in an open position spaced apart from the stationary handle 42. The illustrated handle assembly 40 further comprises a selector 72 operably coupled to the actuation mechanism housed within the handle assembly 40 as further discussed herein. As illustrated in FIG. 3, the selector 72 is in a first position.

Figure 4:
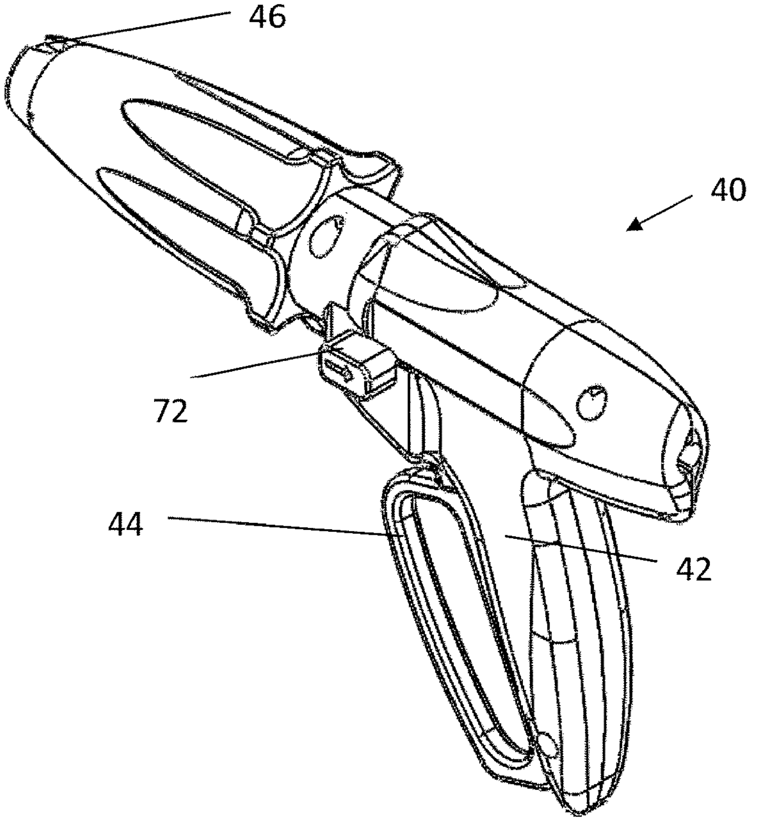
FIG. 4 is a perspective view of the handle assembly of FIG. 3 with a movable handle in a closed configuration.
Figure 5:
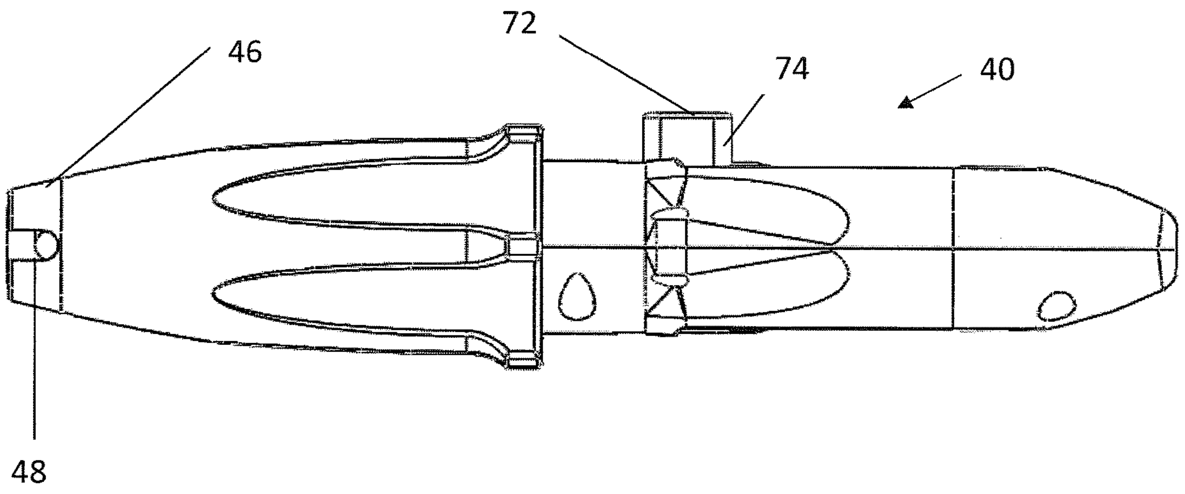
FIG. 5 is a top view of the handle assembly of FIG. 3 with a selector in a first configuration.
Figure 6:
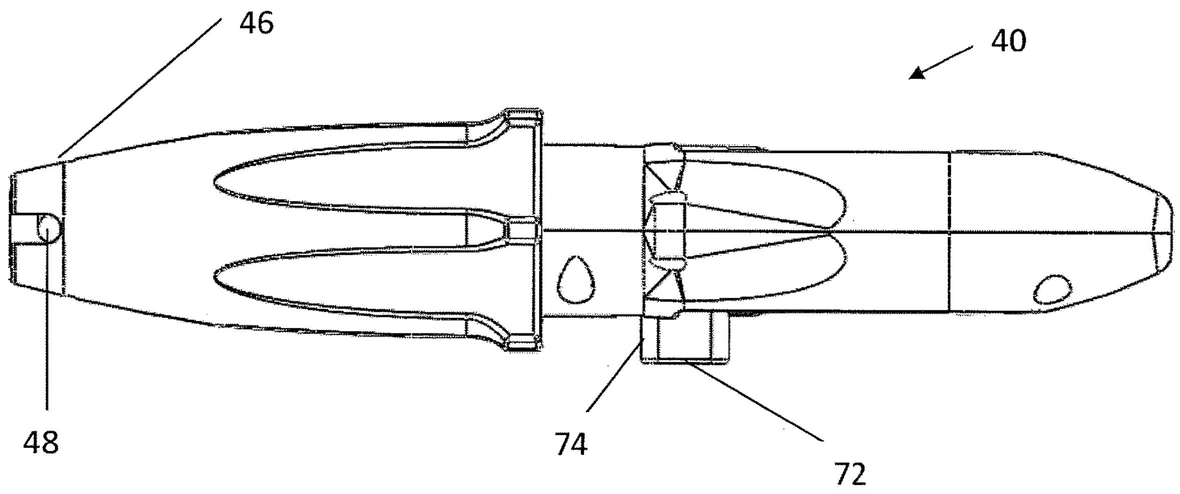
FIG. 6 is a top view of the handle assembly of FIG. 3 with a selector in a second configuration.
Figure 7:
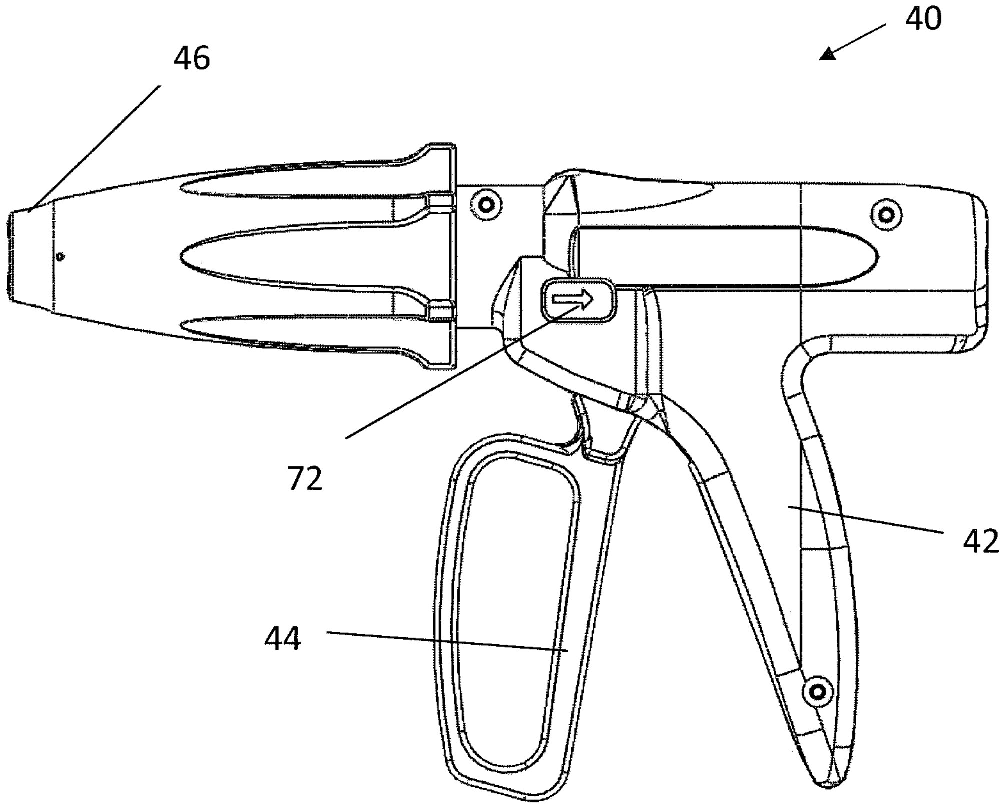
FIG. 7 is a side view of the handle assembly of FIG. 3.

With reference to FIG. 4, another perspective view of the handle assembly 40 of FIG. 3 is illustrated. As illustrated, the movable handle 44 is in a closed position positioned adjacent the stationary handle 42, and the selector 72 is in a second position. FIGS. 5 and 6 illustrate a top view of the handle assembly of FIG. 3 with the selector 72, such as a slider 74, in the first position (FIG. 5), and in the second position (FIG. 6). FIG. 7 illustrates a side view of the handle assembly 40 of FIG. 3.

Figure 8A:
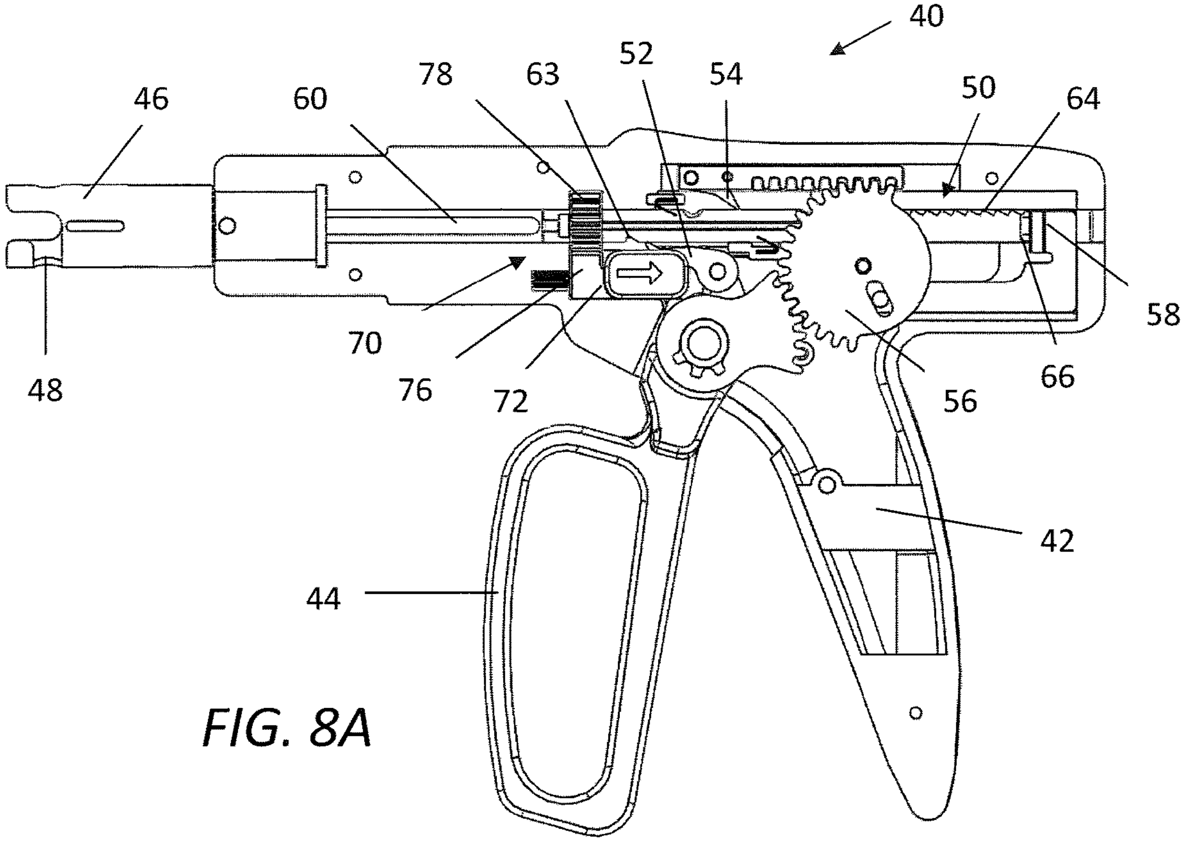
FIG. 8A is a cross-sectional side view of the handle assembly of FIG. 3 in an initial configuration.
Figure 8B:
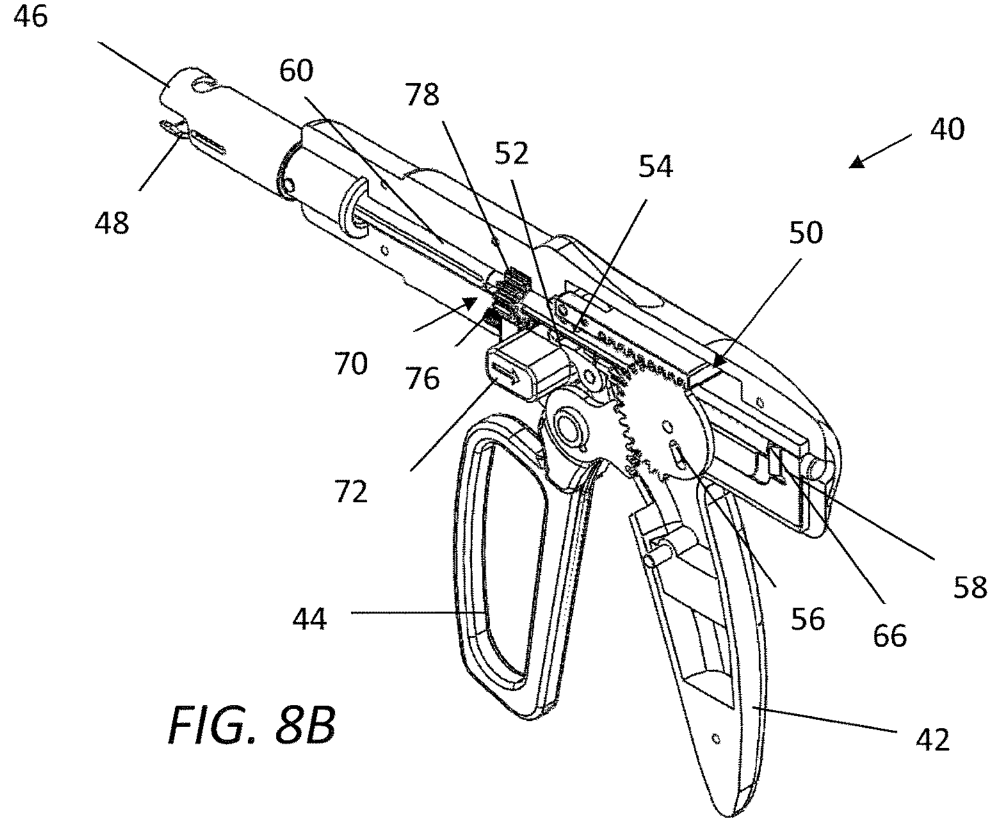
FIG. 8B is a cross-sectional perspective view of the handle assembly of FIG. 8A.

FIGS. 8A and 8B illustrate cross-sectional views of the handle assembly 40 in an initial configuration, revealing operation of the actuation mechanism 50. In the illustrated embodiment, the actuation mechanism 50 is configured to selectively translate the actuation shaft 60 from a first position corresponding to the jaw assembly 30 being in the open configuration to a second position corresponding to the jaw assembly 30 being in the closed configuration and from the second position to a third position to position the jaw assembly 30 in a stapling configuration and deploy the plurality of staples 36. In the initial configuration illustrated in FIGS. 8A and 8B, actuation mechanism 50 can repeatedly translate the actuation shaft 60 between the first position and the second position responsive to movement of the movable handle 44 or trigger without deploying the staples to provide an open and close functionality. This open and close functionality allows a user to position, clamp tissue, and reposition the stapler 10 to find a desirable staple placement location before deploying the staples.

With reference to FIGS. 8-14, in the illustrated embodiment, the actuation mechanism comprises an advancing or forward driver 52, a reverse driver 54, an opening driver 58, an advancing surface 62, a reversing surface 64, and an opening surface 66. The forward driver 52 can be operably coupled to the movable handle 44 such that movement of the movable handle 44 from the open position to the closed position advances the forward driver 52 in a first direction such as for example distally within the handle assembly 40. The forward driver 52 can comprise a pawl or tooth configured to engage a recess or slot.

The reverse driver 54 can be operably coupled to movable handle 44 such that movement of the movable handle 44 from the open position to the closed position advances the reverse driver 54 in a second direction opposite the first direction such as, for example proximally within the handle assembly 40. In some embodiments, the movable handle 44 can be operably coupled with the reverse driver 54 with a geared connection including an idler gear 56. The reverse driver 54 can comprise a pawl or tooth configured to engage a recess or slot.

The opening driver 58 can be operably coupled to the movable handle 44 such that movement of the movable handle 44 from the open position to the closed position advances the opening driver 58 in a first direction such as for example distally within the handle assembly 40. In the illustrated embodiment, the opening driver 58 is coupled to the idler 56 with a pin and slot connection to operably couple the opening driver 58 to the movable handle 44. The opening driver 58 can comprise a pawl or tooth configured to engage a recess or slot.

The actuation shaft 60 includes advancing surface 62, reversing surface 64, and opening surface 66 formed thereon. In the illustrated embodiment, the advancing surface 62 comprises a rack, or plurality of spaced recesses or teeth formed longitudinally along the actuation shaft 60. As illustrated, reversing surface 64 comprises a rack or plurality of space recesses or teeth formed longitudinally along the actuation shaft 60 and angularly offset from the advancing surface 62. In the illustrated embodiment, the opening surface 66 comprises a recess formed in the actuation shaft 60.

In certain embodiments, the actuation shaft 60 is rotatable within the handle assembly 40 about the longitudinal axis of the stapler 10. The handle assembly 40 can comprise a rotation mechanism 70 to provide selective rotation of the actuation shaft 60 within the handle assembly 40. The actuation shaft 60 can be rotatable between a first orientation in which the forward driver 52 is engageable with the advancing surface 62 and a second orientation in which the reverse driver 54 is engageable with the reversing surface 64. With the angular offset of the advancing surface 52 from the reversing surface 54 with respect to the actuation shaft 60, with the actuation shaft in the first orientation, the reverse driver 54 is disengaged from the reversing surface 64, and with the actuation shaft in the second orientation, the forward driver 52 is disengaged from the advancing surface 62.

With continued reference to FIGS. 8-14, in certain embodiments, the rotation mechanism 70 comprises a selector 72, such as a slider. The slider can extend transversely through the housing of the handle assembly 40. The slider can be operably coupled to the actuation shaft 60 such that positioning the slider in the first position extending from one side of the handle assembly 40 positions the actuation shaft 60 in the first orientation, and positioning the slider in the second position extending from an opposite side of the handle assembly 40 rotates the actuation shaft 60 to the second orientation. In the illustrated embodiment, the slider is coupled to a rack 76 in meshing engagement with a gear 78 that is rotatably fixed to the actuation shaft 60 and longitudinally slidable along the actuation shaft 60 (such as, for example, with a keyed connection). Desirably, the illustrated rotation mechanism 70 including a slider discretely positions the actuation shaft 60 in a desired orientation, reducing the incidence of the mismeshed gearing within the actuation mechanism 50. In some embodiments the slider can include visual indicators, such as arrows, to indicate the orientation of the actuation shaft 60, and thus, the actuation mode of the stapler to a user.

In the illustrated embodiment, the advancing surface 62 and the reverse surface 64 are angularly offset by approximately 90 degrees about the actuation shaft. Thus, the rotation mechanism 70 is configured to rotate the actuation shaft approximately 90 degrees between the first orientation and the second orientation. In other embodiments, the actuation surface 62 and the reverse surface 64 can have a different angular offset, such as, for example 120 degrees, and the rotation mechanism 70 can be configured to rotate the actuation shaft 60 correspondingly. Moreover, as described in further detail herein with respect to an open/close mode of the handle assembly 40 operation, in the illustrated embodiment, the opening driver 58 engages with the actuation shaft in the second orientation, in other embodiments, the actuation shaft can be rotatable to a third orientation in which the opening driver 58 engages with the actuation shaft.

With reference to FIGS. 8-14, a typical operation sequence of the actuation mechanism 50 of the handle assembly 40 is illustrated. FIGS. 8A-8B and 9A-9B illustrate operation of the handle assembly 40 in an initial configuration providing an open/close functionality to the jaw assembly 30. In FIG. 8A, the movable trigger 44 is at an open position, and the actuation shaft 60 is at a first position, corresponding to the first position of the actuation beam at the distal end of the elongate shaft 20. In the initial position, the actuation shaft 60 is positioned at the second orientation such that the reverse driver 54 is angularly aligned with the reversing surface 64. With actuation shaft 60 in the second orientation, the opening driver 58 is positioned within the opening surface 66 or recess. Movement of the movable handle 44 from the open position (FIG. 8A-8B) to the closed position (FIG. 9A-9B), advances the forward driver 52 distally along the actuation shaft 60 to engage an advancing recess 63 formed in the actuation shaft 60 and drive the actuation shaft 60 distally in the handle assembly 40 to a second position. The second position of the actuation shaft 60 within the handle assembly 40 corresponds to the second position of the actuation beam, which positions the jaw assembly 30 in a closed configuration.

Figure 11A:
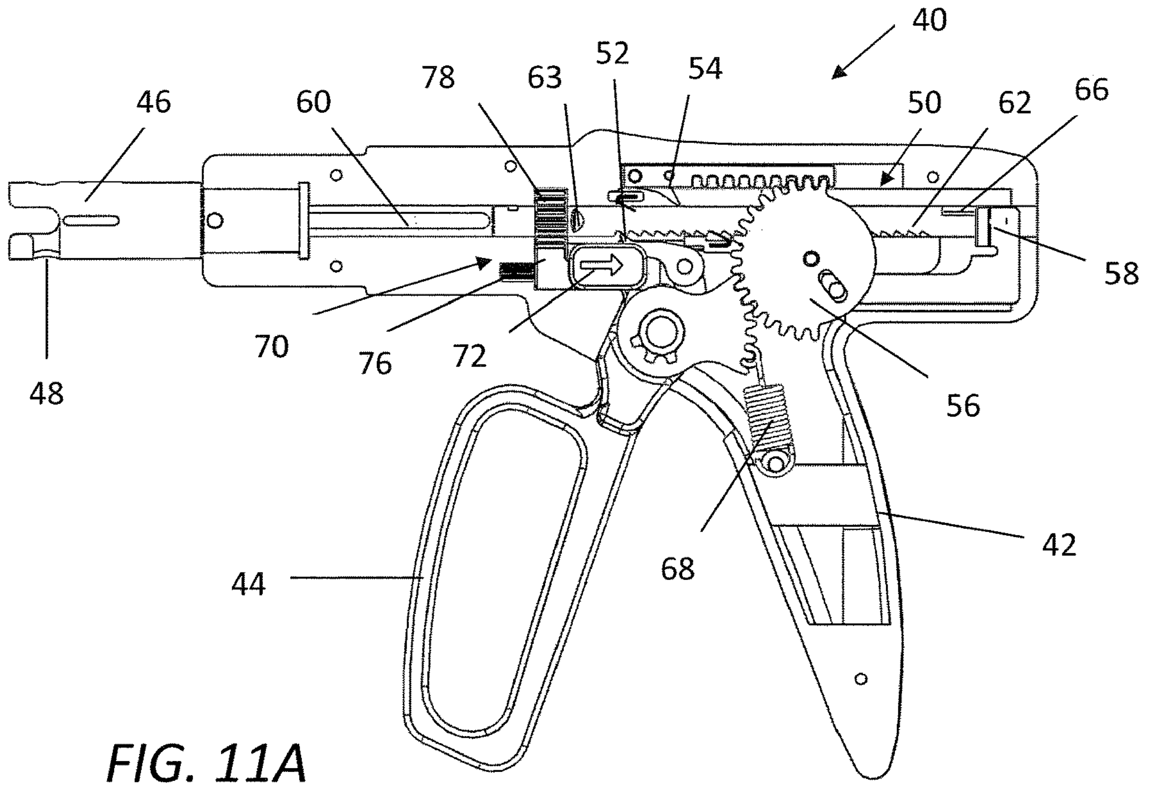
FIG. 11A is a cross-sectional side view of the handle assembly of FIG. 3 in the forward drive configuration.
Figure 11B:
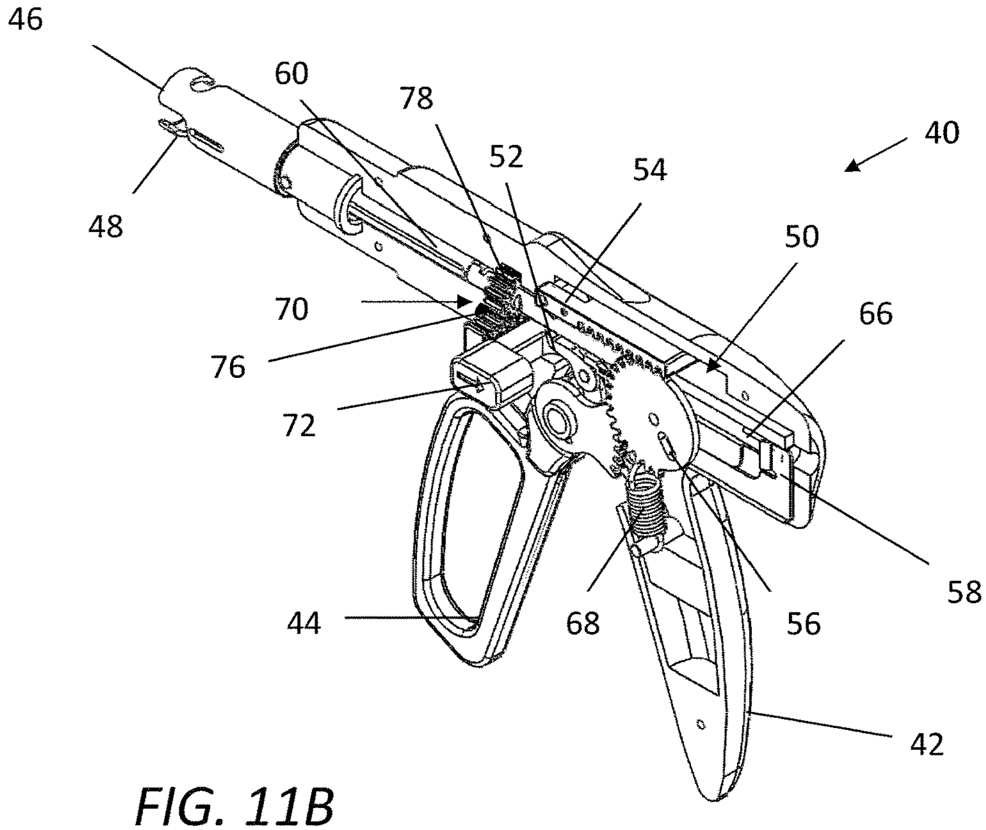
FIG. 11B is a cross-sectional perspective view of the handle assembly of FIG. 11A.

The movable handle 44 can be biased to the open position by a biasing member, such as a coil spring 68 (FIG. 11A). Thus, releasing the movable handle 44 from the closed position illustrated in FIG. 9A-9B would return it to the open position of FIGS. 8A-8B. Operable coupling of the movable handle 44 to the opening driver 58 would likewise translate the opening driver 58 proximally within the handle assembly 40 as the movable handle 44 returns to the open position. In the second orientation of the actuation shaft 60, the opening driver 58 engages opening surface 66 such that the proximal movement of the opening driver 58 returns the actuation shaft 60 from the second position to the first position, returning the jaw assembly 30 to the open configuration.

Figure 9A:
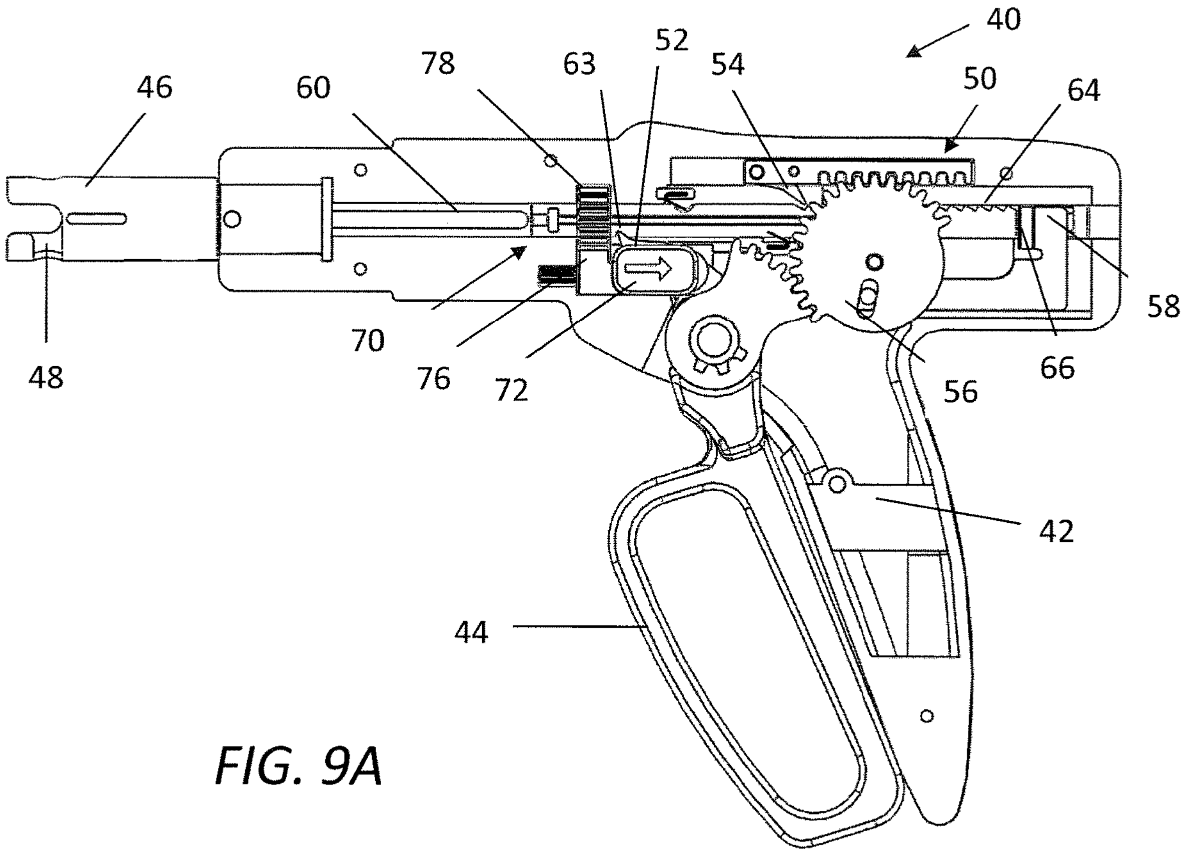
FIG. 9A is a cross-sectional side view of the handle assembly of FIG. 3 actuated to a closed configuration.
Figure 9B:
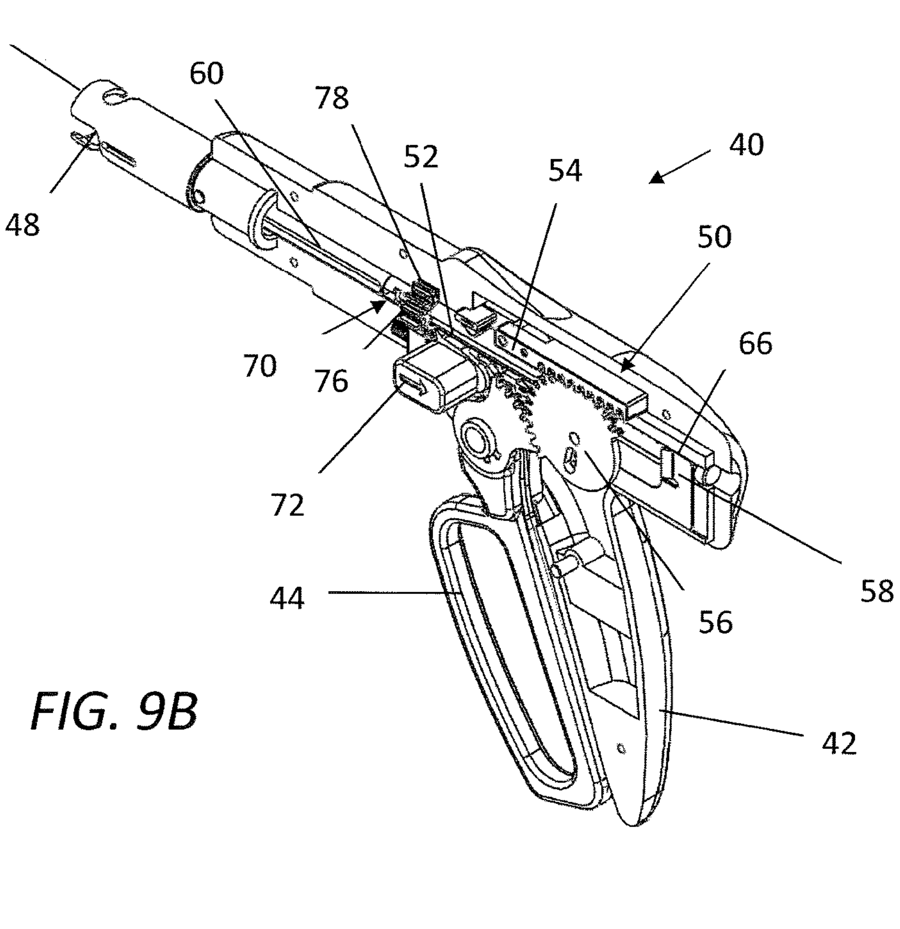
FIG. 9B is a cross-sectional perspective view of the handle assembly of FIG. 9A.
Figure 10A:
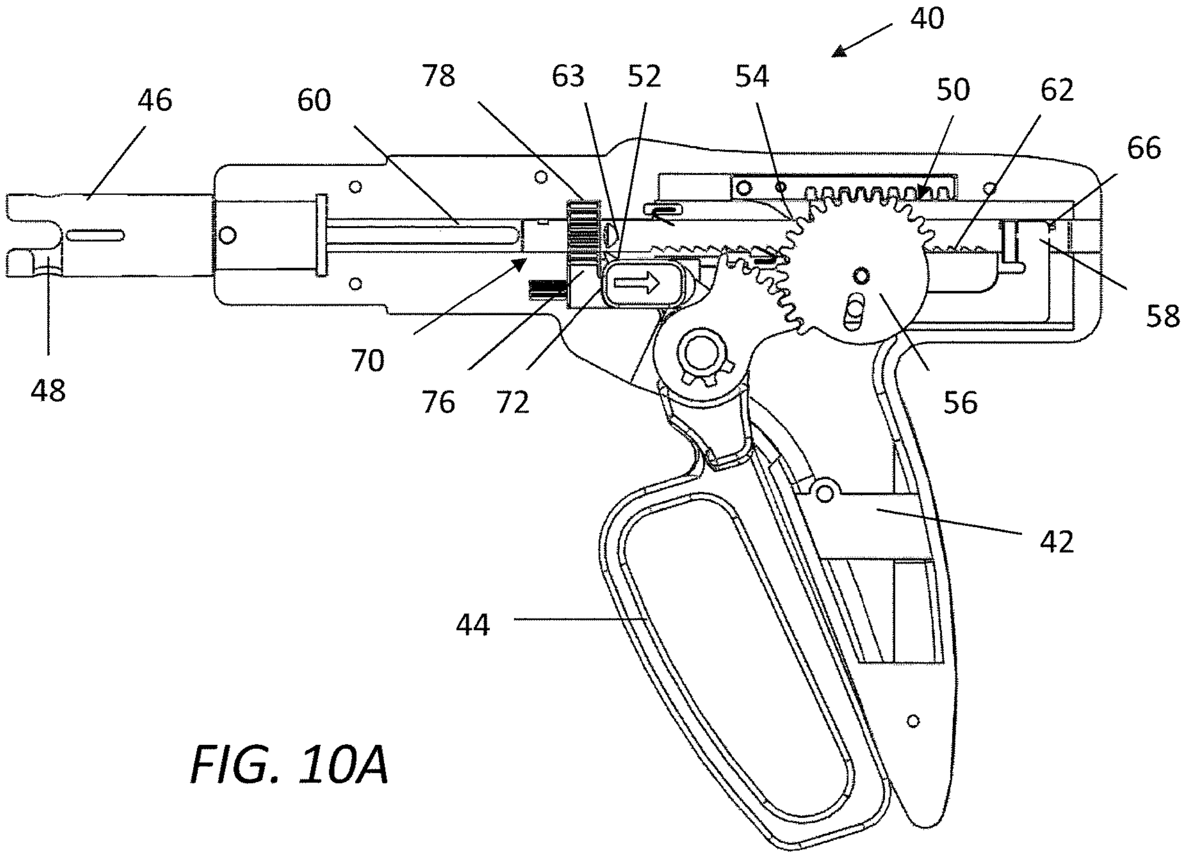
FIG. 10A is a cross-sectional side view of the handle assembly of FIG. 3 in a forward drive configuration.
Figure 10B:
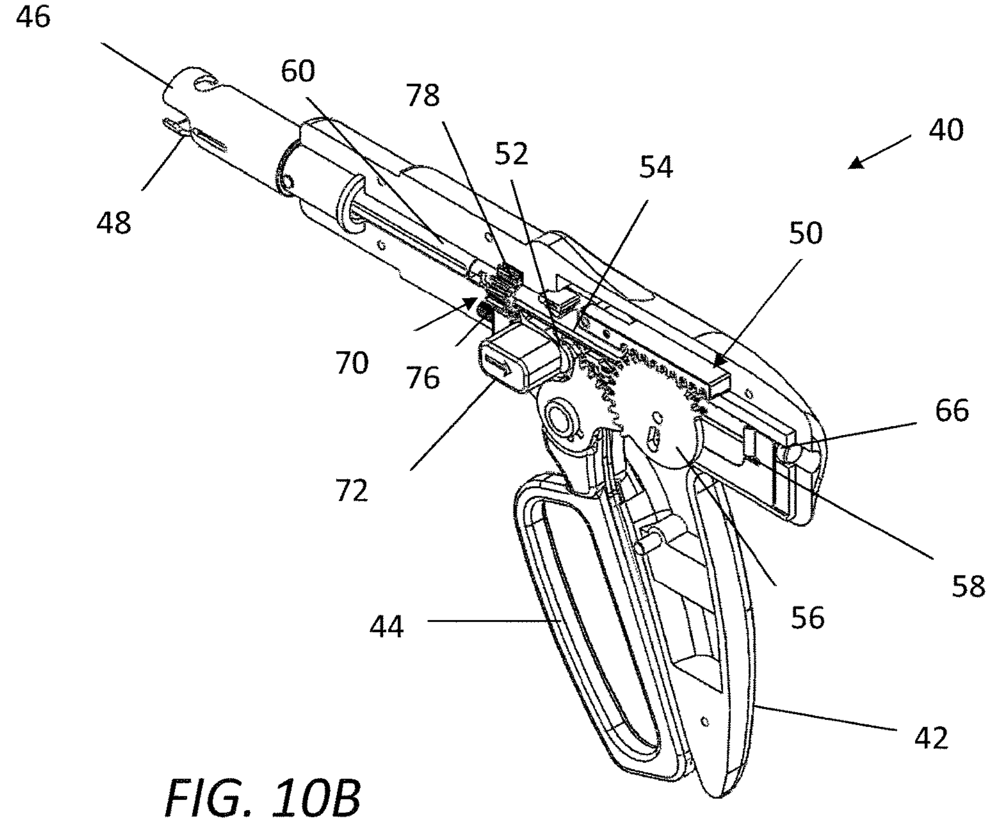
FIG. 10B is a cross-sectional perspective view of the handle assembly of FIG. 10A.

A user can seek a desired stapling position within a surgical field by repeatedly opening and closing the jaws to clamp tissue in various locations. Once a desired stapling position has been selected, the actuation mechanism 50 can be configured in a stapling or firing mode by rotating the actuation shaft 60 to the first orientation. With the jaw assembly a closed configuration at a desired stapling position (as illustrated in FIGS. 9A-9B), a user can reposition the selector 72 by sliding the slider to the first position, corresponding to the first orientation of the actuation shaft 60 (as illustrated in FIGS. 10A-10B). In the first orientation of the actuation shaft 60, the forward driver 52 is engageable with the advancing surface 62, the reversing driver 54 is angularly misaligned with the reversing surface 64, and the opening driver 58 angularly misaligned with the opening surface 66. With the actuation shaft 60 in the first orientation, the movable handle 44 can be released into the open position (FIG. 11A-11B), engaging the forward driver 52 with the advancing surface 62.

Figure 12A:
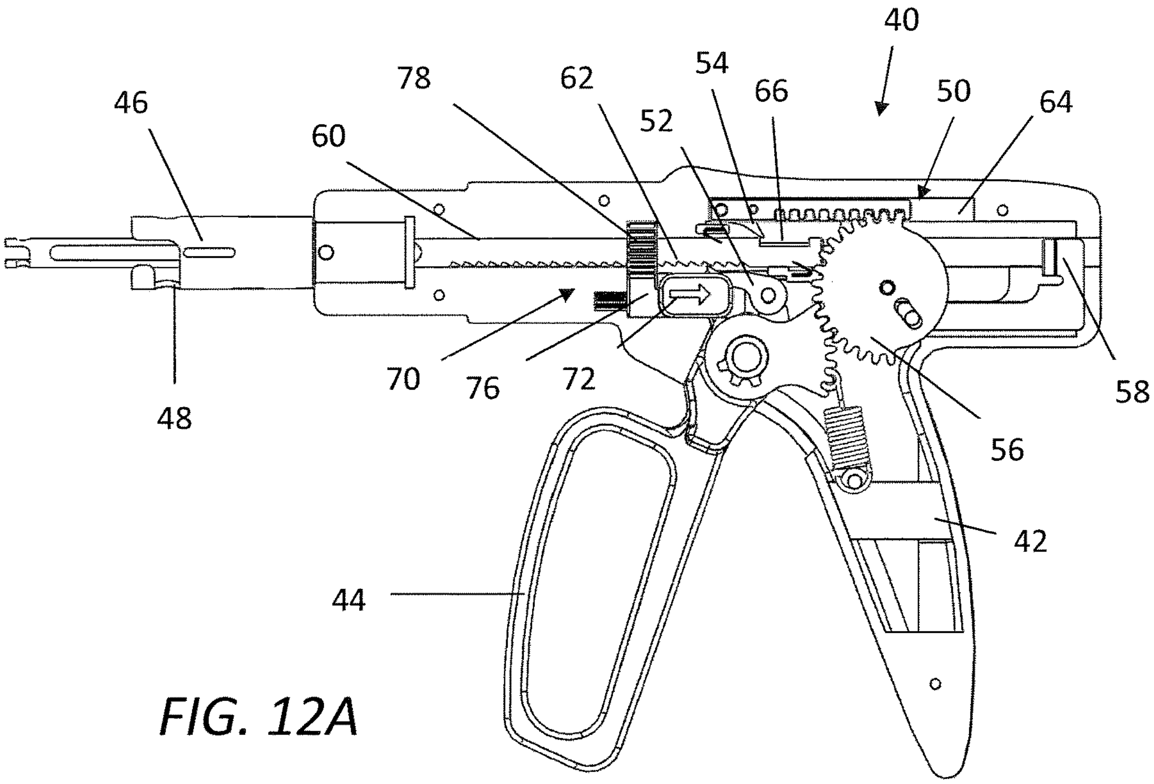
FIG. 12A is a cross-sectional side view of handle assembly of FIG. 3 in a fully driven forward configuration.
Figure 12B:
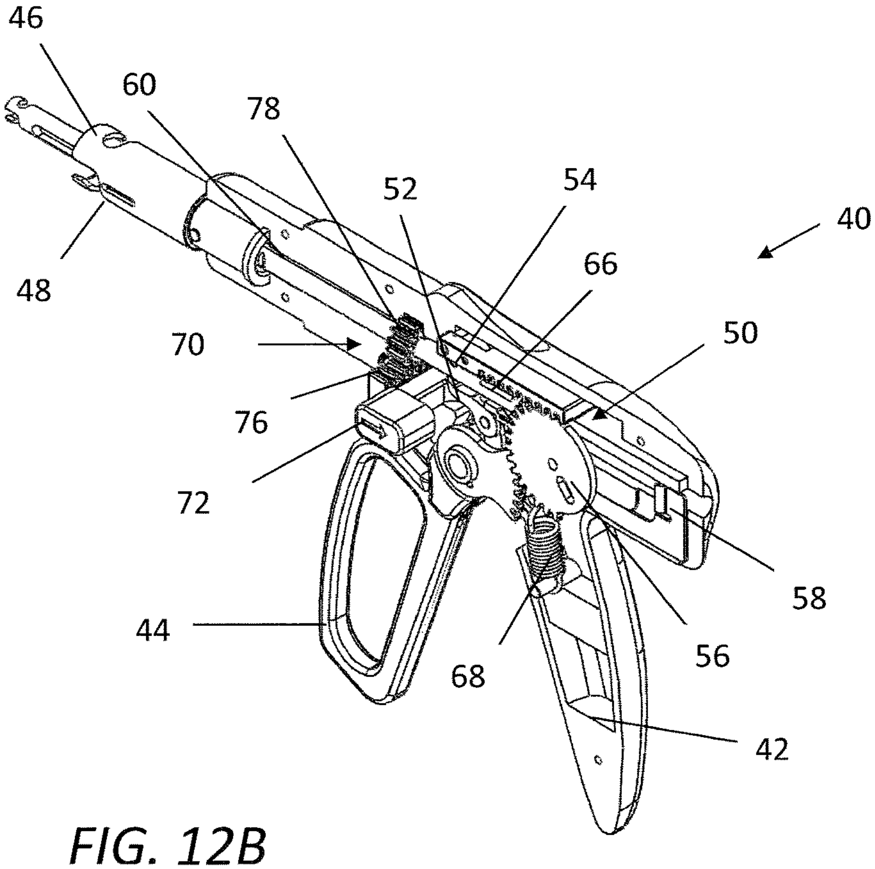
FIG. 12B is a cross-sectional perspective view of the handle assembly of FIG. 12A.

With reference to FIGS. 11A-11B and 12A-12B, with the actuation shaft 60 in the first orientation, and the forward driver 52 engaging the advancing surface 62, the actuation mechanism 50 is in a stapling or firing mode. Several cycles of movable handle 44 movement from the open position to the closed position and back to the open position advance the actuation shaft 60 from the second position (FIGS. 11A-11B), to a third position in which the actuation shaft 60 is moved to its distal-most limit with respect to the handle assembly 40 (FIGS. 12A-12B). In some embodiments, the actuation mechanism can include a stop to interfere with distal travel of the actuation shaft 60 at the third position. The second position of the actuation shaft corresponds to the second position of the actuation beam in the jaw assembly 30. The third position of the actuation shaft corresponds to the third position of the actuation beam in the jaw assembly 30 in which the plurality of staples have been deployed from the first jaw. With movement of the movable handle 44 or trigger in the firing mode to advance the actuation shaft from the second position to the third position, the forward driver 52 is sequentially advanced over the adjacent teeth or grooves of the actuating surface 62 in a ratchet-like advancement.

Figure 13A:
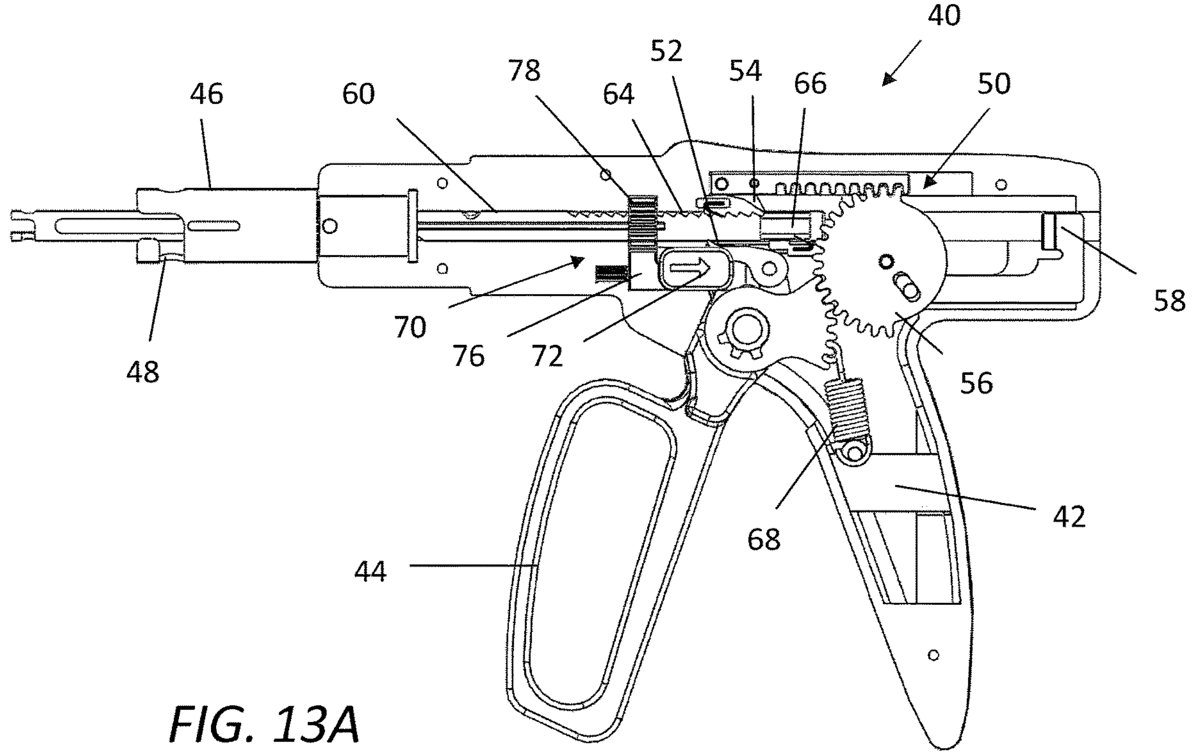
FIG. 13A is a cross-sectional side view of the handle assembly of FIG. 3 in a reverse drive configuration.
Figure 13B:
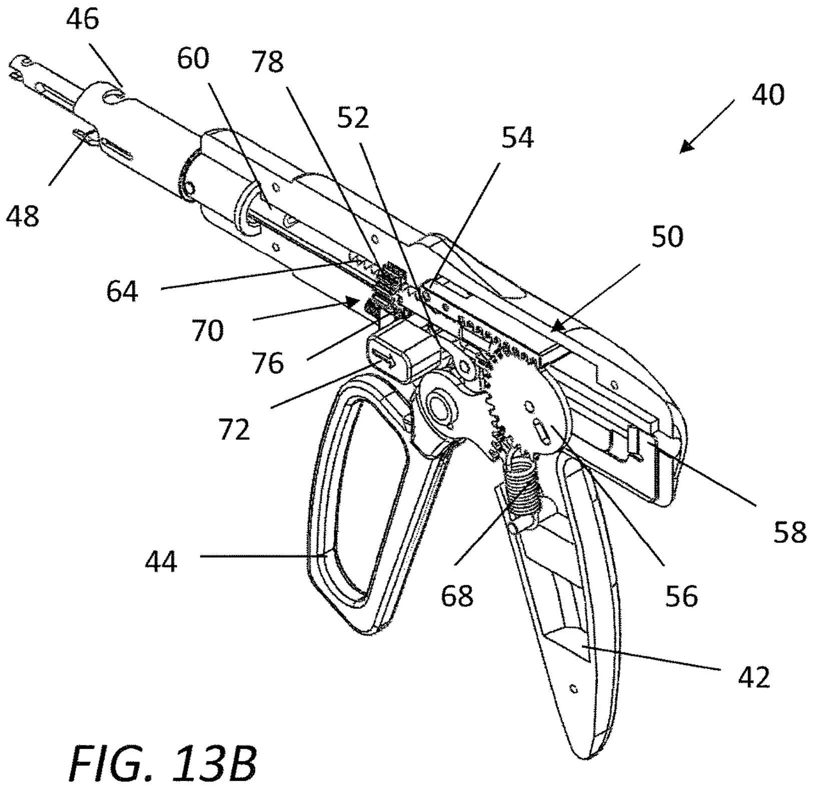
FIG. 13B is a cross-sectional perspective view of the handle assembly of FIG. 13A.
Figure 14A:
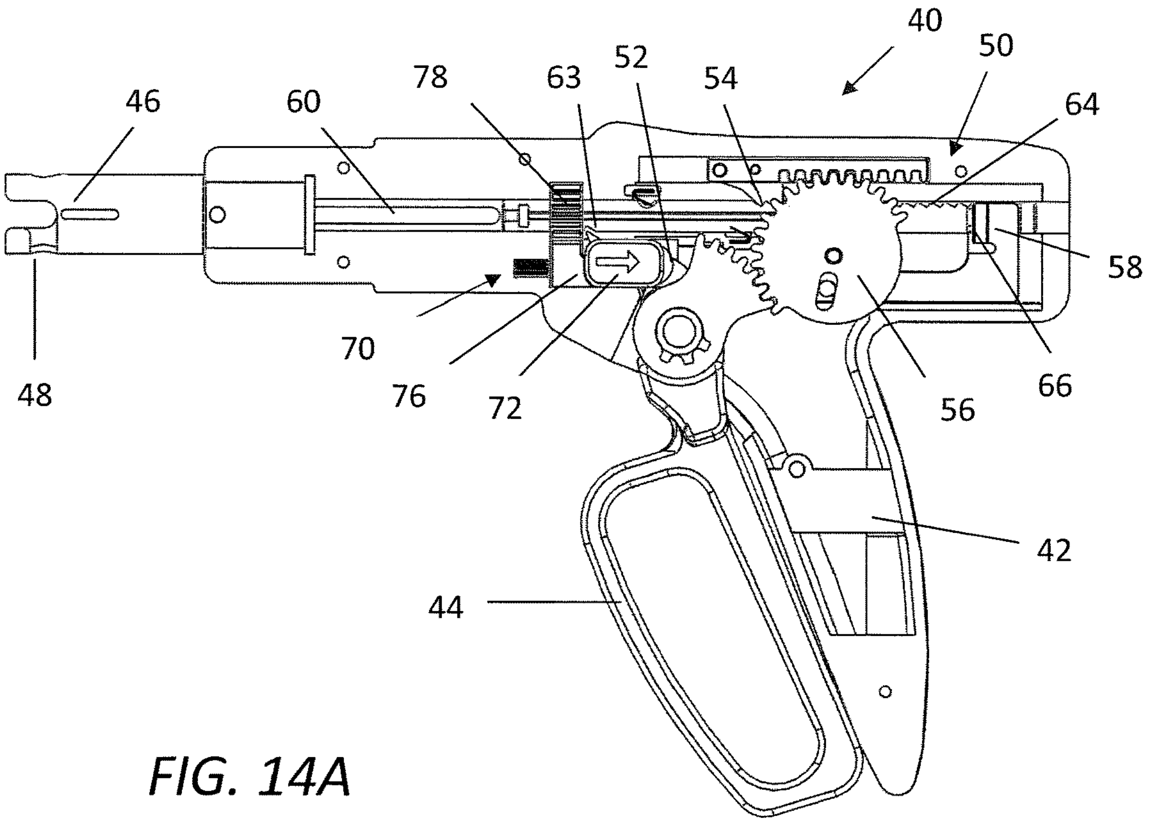
FIG. 14A is a cross-sectional side view of the handle assembly of FIG. 3 in a fully driven reverse configuration.
Figure 14B:
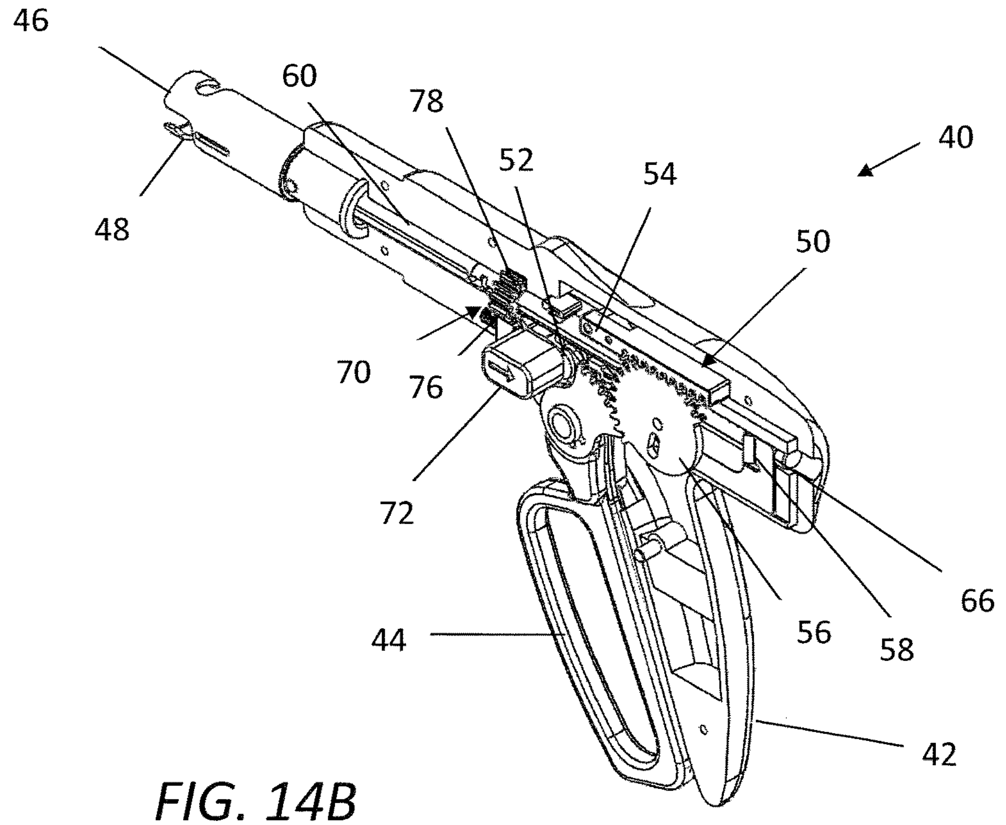
FIG. 14B is a cross-sectional perspective view of the handle assembly of FIG. 14A.

With reference to FIGS. 13A-13B, once the actuation shaft 60 has been advanced to the third position and the staples have been fired from the jaw assembly, the actuation mechanism 50 can be configured in a reverse mode. Accordingly, the rotation mechanism 70 can rotate the actuation shaft 60 to the second orientation to position the reversing surface 64 in angular alignment with the reverse driver 54. The slider can be slid to the second position to rotate the actuation shaft from the first orientation (FIGS. 12A-12B) to the second orientation (FIGS. 13A-13B). With the actuation shaft 60 in the second orientation, repeated cycles of the movable handle 44 from the open position to the closed position and back to the open position engage the reverse driver 54 with the reversing surface 64 in a ratchet-like advancement while retracting the actuation shaft 60 proximally in the handle assembly 40. Once the reverse driver 54 has driven the actuation shaft 60 proximally to the second position (illustrated in FIGS. 14A-14B), the opening driver 58 engages the opening surface 66. The opening driver 58 returns the actuation shaft 60 to the first position when the movable handle 44 is released to the open position. (Returning the handle assembly to the configuration illustrated in FIGS. 8A-8B). With the actuation shaft 60 in the first position, the cartridge, emptied of staples, can be decoupled from the handle assembly 40 and a new cartridge can be coupled to the handle assembly to begin another stapling operation.

Figure 15:
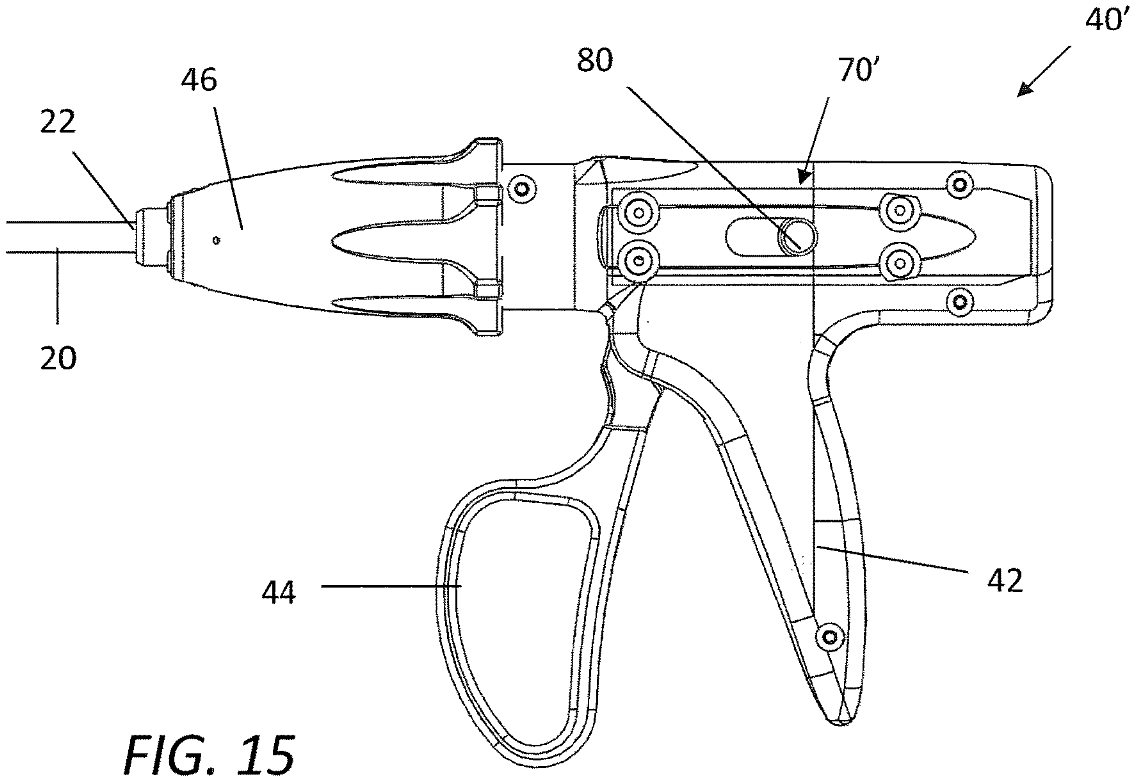
FIG. 15 is a side view of another embodiment of handle assembly for a surgical stapling device.
Figure 16:
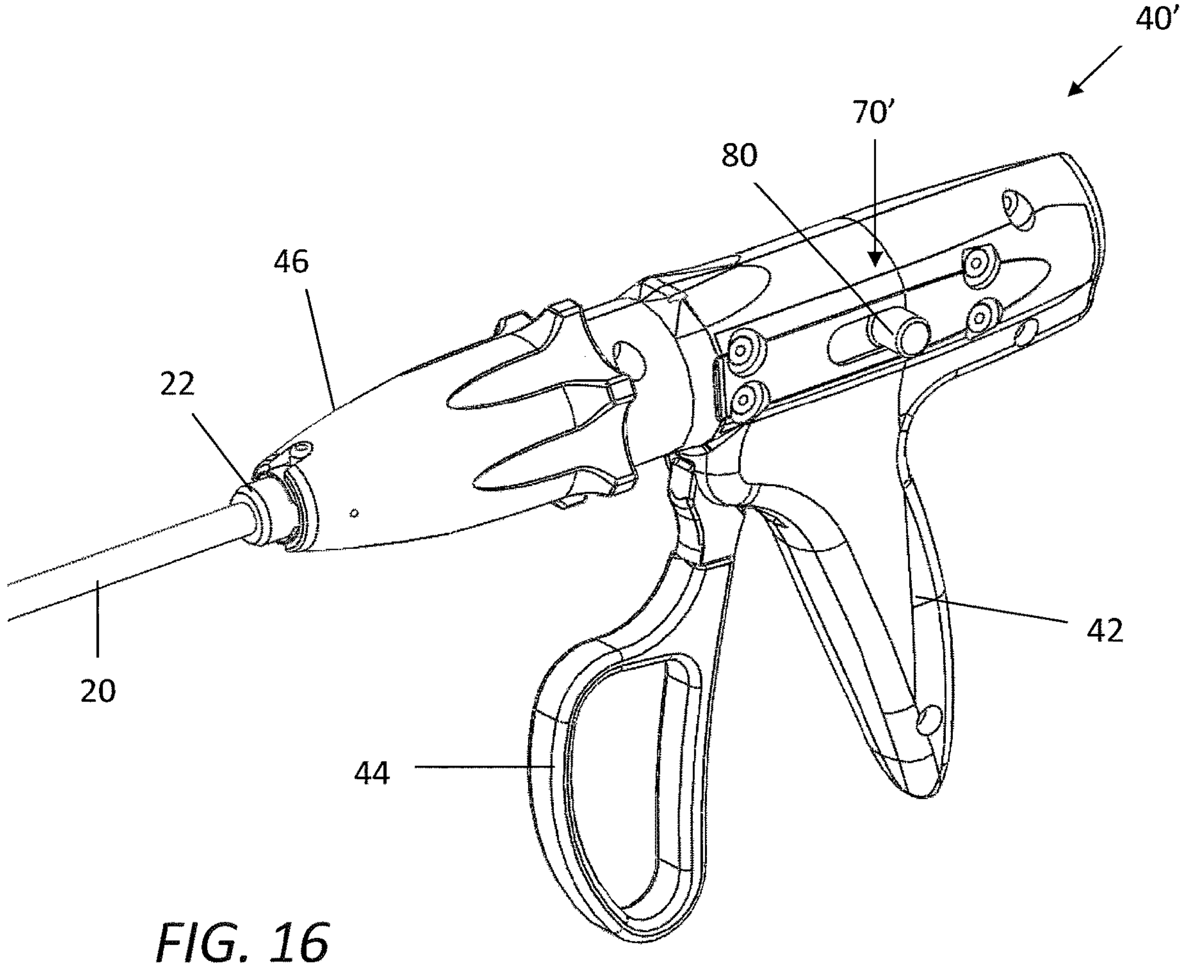
FIG. 16 is a perspective view of the handle assembly of FIG. 15.

With reference to FIGS. 15-25, another embodiment of handle assembly 40' for use with a surgical stapler 10' is illustrated. FIG. 15 illustrates a side view of the handle assembly 40', and FIG. 16 illustrates a perspective view of the handle assembly 40'. In the handle assembly 40', actuation of the rotation mechanism 70' is accomplished with a slidable switch 80 that is longitudinally slidable with respect to the handle assembly 40' housing. Advantageously, such a slidable switch arrangement can allow a user to easily rotate the actuation shaft 60 in a single-handed operation.

Figure 17:
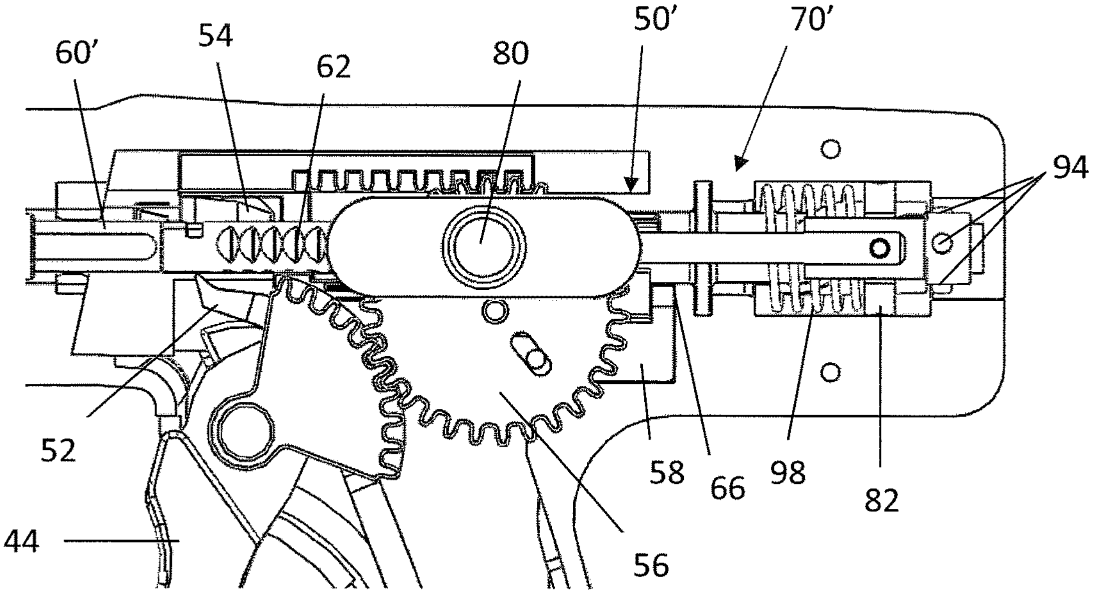
FIG. 17 is a cutaway side view of the handle assembly of FIG. 15.

With reference to FIG. 17, a cross-sectional view of the handle assembly 40' is illustrated revealing the actuation mechanism 50' and the rotation mechanism 70'. The actuation mechanism functions substantially as described above with respect to the embodiment of FIGS. 8A, 8B-14A, 14B to advance the actuation shaft 60' from a first position to a second position in an open/close mode, from the second position to a third position in a stapling mode, and from the third position to the first position in a reverse mode. The actuation mechanism 50' includes corresponding forward, reverse, and opening drivers 52, 54, 58 operably coupled to a movable handle 44 and advancing 62, reversing, and opening surfaces on the actuation shaft 60' substantially as described with respect to the embodiment of FIGS. 8A, 8B-14A-14B. However, in the embodiment illustrated in FIGS. 15-25, the actuation shaft 60' is rotatable by the rotation mechanism 70' discretely between a first orientation corresponding to the open/close mode of the handle assembly wherein the opening driver 58 engages the opening surface 66, a second orientation corresponding to the stapling position, wherein the forward driver 52 engages the advancing surface 62, and a third orientation corresponding to the reverse position wherein the reverse driver 54 engages the reversing surface.

Figure 18:
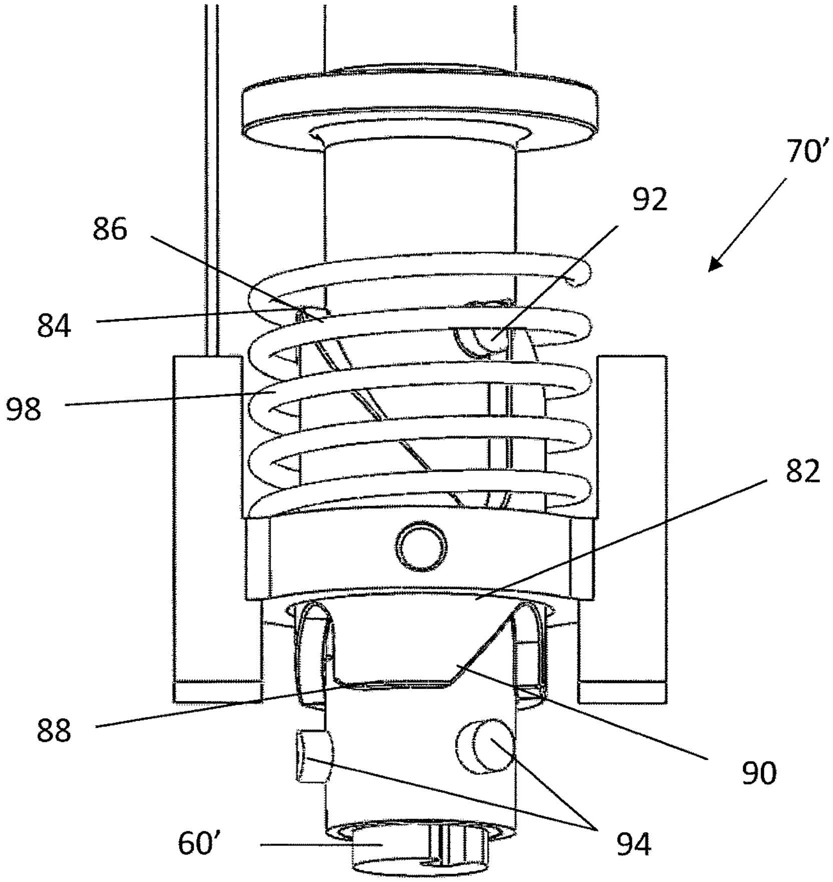
FIG. 18 is a top view of a rotation mechanism for an actuation mechanism of the handle assembly of FIG. 15.

With reference to FIGS. 17-18, certain aspects of the rotation mechanism 70' are illustrated. The rotation mechanism 70' comprises the slidable switch 80 longitudinally slidable with respect to the housing of the handle assembly 40', a hub collar 82 longitudinally slidable by the switch 80, and a biasing member or spring 98. In the illustrated embodiment, the slidable switch 80 is connected to the hub collar 82 with a thin beam, such as a shim member. The hub collar 82 is rotationally fixed and longitudinally slidable with respect to the housing of the handle assembly 40'. In some embodiments, the hub collar 82 can comprise first and second wings that can slide in corresponding first and second slots in the housing of the handle assembly to allow relative longitudinal movement and restrict relative rotational movement therebetween.

The hub collar 82 can be a generally tubular member disposed around the actuation shaft 60'. The hub collar 82 can extend between a first edge 84 having a plurality of ramps 86 formed therein and a second edge 88 having a plurality of recesses 90 formed therein. In the illustrated embodiment, the hub collar 82 comprises three ramps 86 formed in the first edge 84 with each ramp spaced approximately 120 degrees apart from adjacent ramps 86. As illustrated, the hub collar 82 comprises three recesses 90 formed in the second edge 88 with each recess 90 being approximately 120 degrees apart from adjacent recesses 86. In other embodiments, the number and relative spacing of ramps 86 and recesses 90 can vary to rotate the actuation shaft 50 between different orientations from those of the illustrated embodiment.

In some embodiments, the rotation mechanism 70' can include a spring 98 to bias the slidable switch 80 and the hub collar 82 to a proximal position with respect to the housing of the handle assembly 40'.

With continued reference to FIGS. 17-18, the actuation shaft 60' can have a first plurality of projections 92 projecting radially outwardly therefrom adjacent the first edge 84 of the hub collar 82. In the illustrated embodiment, the actuation shaft has three projections 92 each spaced approximately 120 degrees from the adjacent projections. The actuation shaft 60' can further comprise a second plurality of projections 94 extending radially outwardly from the actuation shaft 60' at a position adjacent the second edge 88 of the hub collar 82. In the illustrated embodiment, the actuation shaft 60' has three projections 94 each spaced approximately 120 degrees from the adjacent projections. In other embodiments, the numbers and spacing of the projections 92, 94 can be varied to achieve a rotation mechanism with different rotational characteristics. In some embodiments, the projections 92, 94 can be formed on the actuation shaft 60', while in other embodiments, the projections 92, 94 can be formed separately such as on a sleeve that is adhered to, has a keyed engagement with, or is otherwise rotationally fixed to the actuation shaft 60'.

Figure 19:
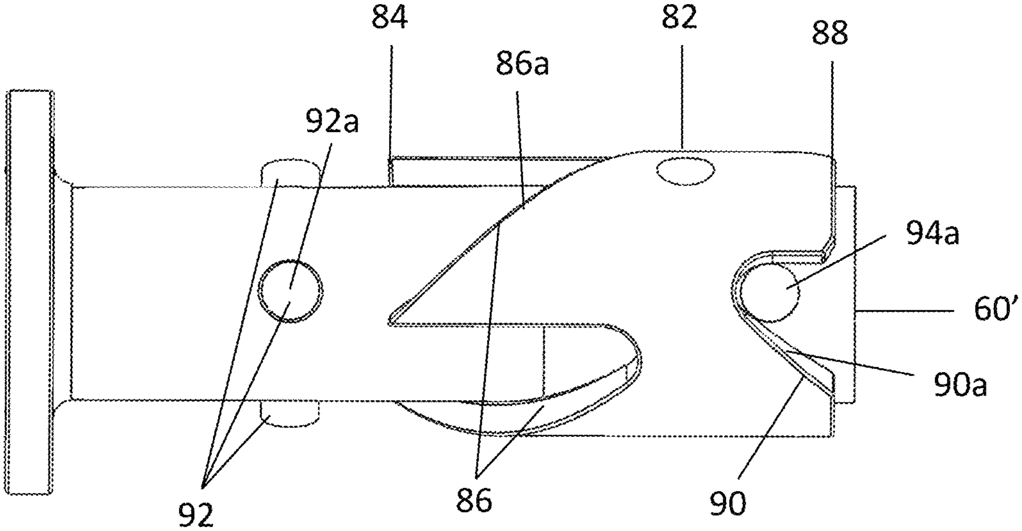
FIG. 19 is a top view of a hub collar and actuation shaft of the rotation mechanism of FIG. 18 with the hub collar in a first position.
Figure 20:
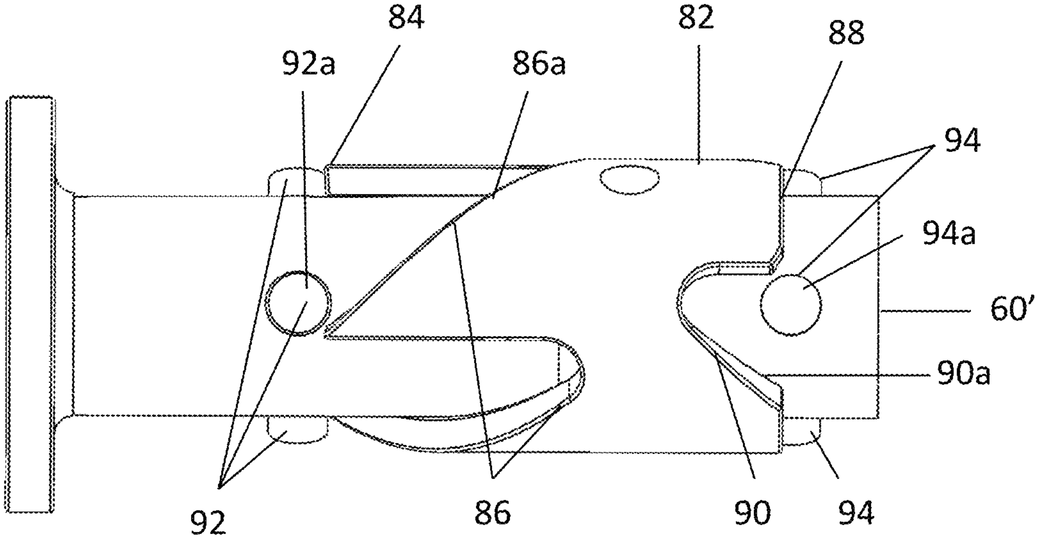
FIG. 20 is a top view of the hub collar and actuation shaft of the rotation mechanism of FIG. 18 with a hub collar in a second position.
Figure 21:
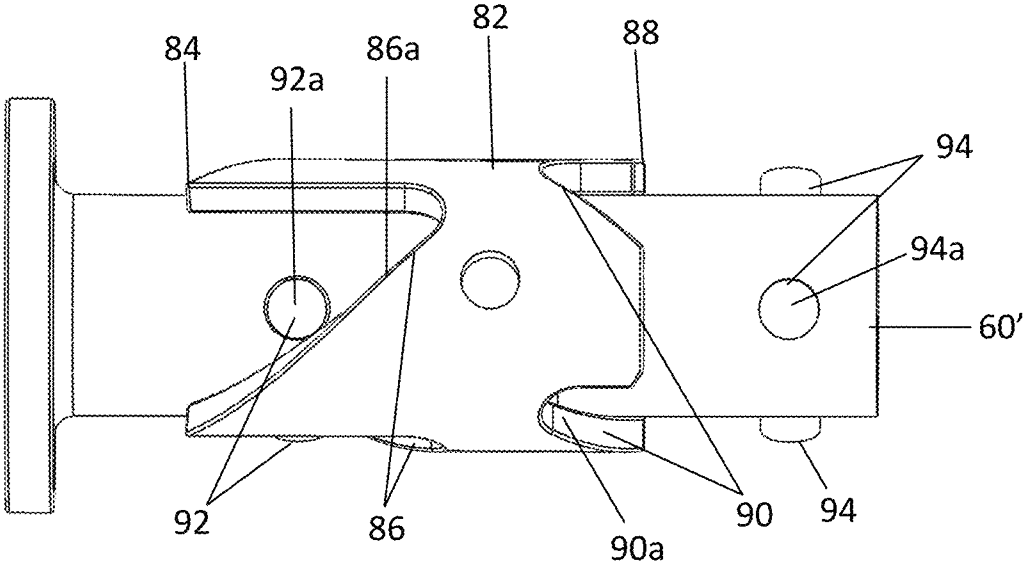
FIG. 21 is a top view of the hub collar and actuation shaft of the rotation mechanism of FIG. 18 with a hub collar in a third position.
Figure 22:
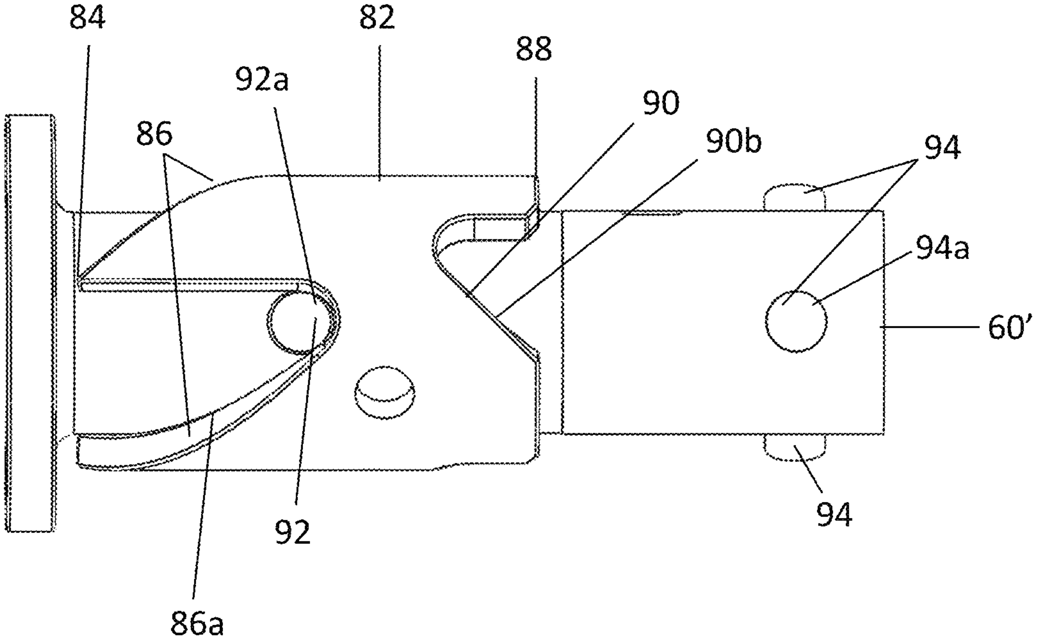
FIG. 22 is a top view of the hub collar and actuation shaft of the rotation mechanism of FIG. 18 with a hub collar in a fourth position.
Figure 23:
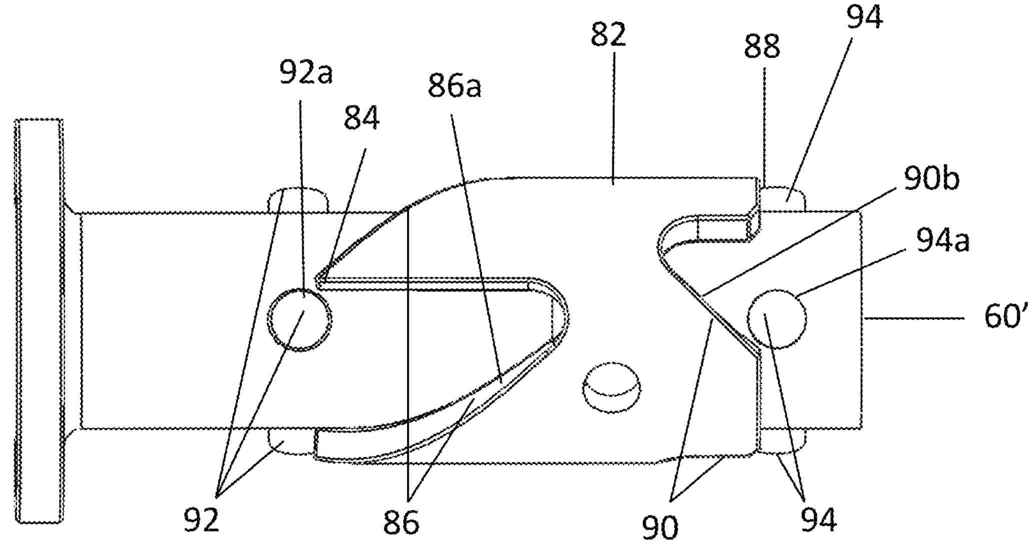
FIG. 23 is a top view of the hub collar and actuation shaft of the rotation mechanism of FIG. 18 with a hub collar in a fifth position.
Figure 24:
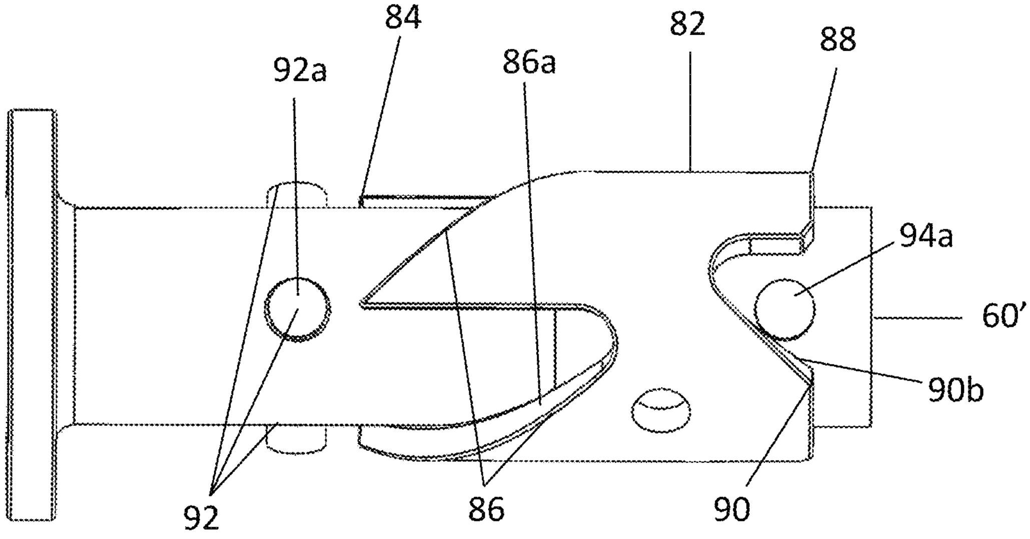
FIG. 24 is a top view of the hub collar and actuation shaft of the rotation mechanism of FIG. 18 with a hub collar in a sixth position.

With reference to FIGS. 19-25, an operation sequence of the rotation mechanism 70' to rotate the actuation shaft 60' from a first orientation to a second orientation is illustrated. FIG. 19 illustrates a schematic view of the hub collar 82 and actuation shaft 50' in a first orientation. In the first orientation, a first projection 94*a* of the second plurality of projections 94 rests in a first recess 90*a* of the plurality of recesses 90, and a first projection 92*a* of the first plurality of projections is positioned adjacent a first ramp 86*a* of the plurality of ramps 86.

Figure 25:
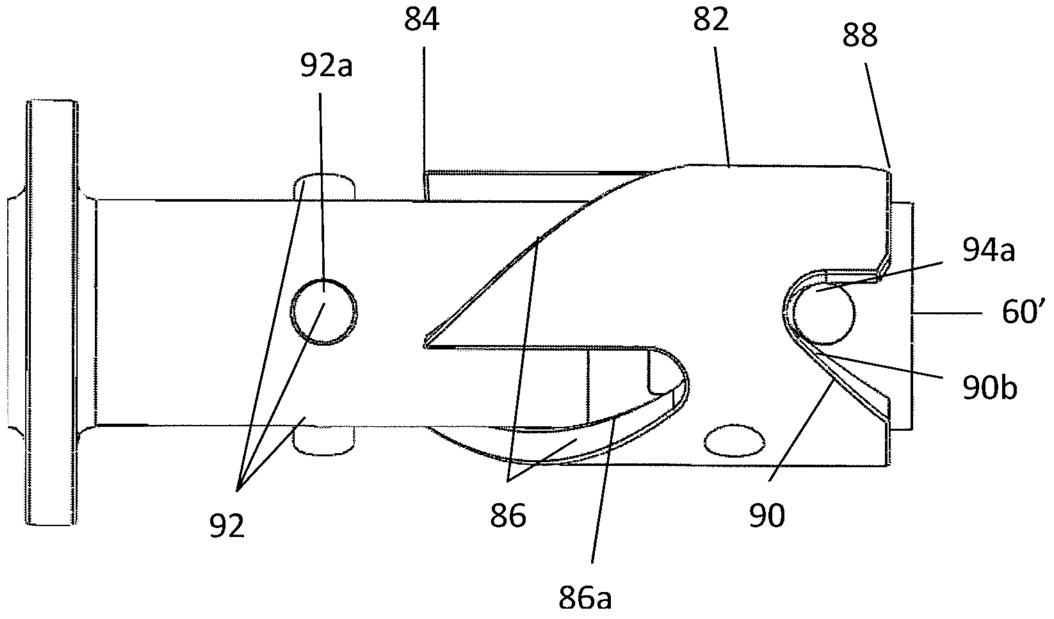
FIG. 25 is a top view of the hub collar and actuation shaft of the rotation mechanism of FIG. 18 with a hub collar in a seventh position.

With reference to FIGS. 19-22, an operation sequence of the rotation mechanism 70' as the slidable switch 80 is advanced distally is illustrated. As the slidable switch 80 is advanced distally with respect to the housing of the handle assembly, the hub collar 82 translates distally, bringing the first plurality of projections 92 into sliding engagement with the plurality of ramps 86 of the hub collar 82 (illustrated in FIG. 20). Further distal advancement of the slidable switch 80 and hub collar 82 relative to the housing of the handle assembly advances the first plurality of projections 92 over the plurality of ramps 86 (illustrated in FIGS. 21 and 22). An angular profile of the ramps 86 acts as a camming surface such that travel of the first plurality of projections 92 along the plurality of ramps 86 rotates the actuation shaft 60'. Once the slidable switch reaches the distal most end of its travel, the spring 98 biases the hub collar 82 and sliding switch 80 proximally with respect to the housing of the handle assembly 40. As the hub collar 82 returns to a proximal position, the second plurality of projections 94 engages the plurality of recesses 90 (illustrated in FIGS. 23-25). As illustrated in FIG. 25, following an actuation cycle of the slidable switch 80, the first projection 94*a* of the second plurality of projections 94 has been positioned in the second recess 90*b* of the plurality of recesses such that the actuation shaft 60' has been positioned in a second orientation rotated 120 degrees from the first orientation. Subsequent actuation cycles of the slidable switch 80 rotate the actuation shaft in discrete 120 degree increments.

In other embodiments, the rotation mechanism can comprise a handle directly connected to the actuation shaft. For example, a proximal end of the actuation shaft can be connected to a handle 70" (FIG. 1) extending proximally from the housing. Rotation of the handle relative to the longitudinal axis rotates the actuation shaft to configure the handle assembly in one of an open/close mode, a forward mode, or a reverse mode.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A handle assembly for a surgical stapler, the handle assembly comprising:
- a stationary handle;
- a movable trigger pivotably coupled to the stationary handle;
- an open driver coupled to the movable trigger; and
- an actuation shaft having a longitudinal axis, the actuation shaft longitudinally slidable along the longitudinal axis within the handle assembly responsive to pivotal movement of the movable trigger and rotatable between a first orientation and a second orientation relative to the longitudinal axis;
- wherein in an initial configuration, the actuation shaft is in the second orientation and the open driver is engaged with the actuation shaft such that movement of the movable trigger relative to the stationary handle longitudinally slides the actuation shaft between a first position and a second position distal the first position; and
- wherein in a firing configuration, the open driver is disengaged from the actuation shaft, the actuation shaft is in the first orientation and movement of the trigger moves the actuation shaft distally of the second position towards a third position distal the second position.

2. The handle assembly of claim 1, further comprising a rotation mechanism configured to rotate the actuation shaft between the first orientation and the second orientation.

3. The handle assembly of claim 1, wherein with the actuation shaft in the initial configuration, the actuation shaft is repeatably slidable between the first position and the second position.

4. The handle assembly of claim 1, wherein with the actuation shaft in the firing configuration, movement of the movable trigger sequentially distally advances the actuation shaft.

5. The handle assembly of claim 4, further comprising an advancing driver coupled to the movable trigger, and wherein in the firing configuration, the advancing driver is coupled to the actuation shaft.

6. The handle assembly of claim 1, wherein with the actuation shaft between the second position and the third position, the actuation shaft is positionable in a reverse configuration in which the actuation shaft is in the second orientation and movement of the trigger moves the actuation shaft proximally from the third position towards the first position.

7. The handle assembly of claim 6, further comprising a reversing driver coupled to the movable trigger, and wherein in the reverse configuration, the reversing driver is coupled to the actuation shaft.

8. The handle assembly of claim 1, further comprising an advancing driver coupled to the movable trigger, a gear coupled to the trigger, and a reversing driver coupled to the gear.

9. The handle assembly of claim 8, wherein the advancing driver is engageable with the actuation shaft and the reversing driver is disengaged from the actuation shaft with the actuation shaft in the first orientation.

10. The handle assembly of claim 9, wherein the advancing driver is disengaged from the actuation shaft and the reversing driver is engageable with the actuation shaft with the actuation shaft in the second orientation.

11. A handle assembly for a surgical stapler, the handle assembly comprising:
- a housing;
- a movable handle pivotably coupled to the housing and movable from an open position to a closed position; and
- an actuation shaft having a longitudinal axis, the actuation shaft comprising an advancing rack and a reversing rack formed therein; the actuation shaft being longitudinally slidable relative to the housing and selectively rotatable about the longitudinal axis between a first orientation in which the advancing rack is coupled to the movable handle and a second orientation in which the reversing rack is coupled to the movable handle.

12. The handle assembly of claim 11, wherein the advancing rack is angularly offset from the reversing rack relative to the longitudinal axis.

13. The handle assembly of claim 12, wherein the advancing rack is angularly offset from the reversing rack by approximately 90 degrees.

14. The handle assembly of claim 11, further comprising a forward driver movable by the movable handle, the forward driver engaged with the advancing rack with the actuation shaft in the first orientation.

15. The handle assembly of claim 14, further comprising a reverse driver coupled to the forward driver, the reverse driver engaged with the reversing rack with the actuation shaft in the second orientation.

16. The handle assembly of claim 15, wherein the reverse driver is disengaged from the actuation shaft with the actuation shaft in the first orientation.

17. The handle assembly of claim 15, wherein the forward driver is coupled to the reverse driver such that movement of the movable handle moves the forward driver in a first direction and moves the reverse driver in a second direction opposite the first direction.

* * * * *